US008357148B2

(12) United States Patent
Boulais et al.

(10) Patent No.: US 8,357,148 B2
(45) Date of Patent: Jan. 22, 2013

(54) MULTI-FUNCTIONAL ENDOSCOPIC SYSTEM FOR USE IN ELECTROSURGICAL APPLICATIONS

(75) Inventors: Dennis R. Boulais, Danielson, CT (US); Michael S. Banik, Bolton, MA (US); Vincent Turturro, Bolton, MA (US); Christopher Rowland, Hopkinton, MA (US); David Hoffman, Westborough, MA (US); John P. O'Connor, Andover, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 437 days.

(21) Appl. No.: 11/238,649

(22) Filed: Sep. 29, 2005

(65) Prior Publication Data

US 2006/0106281 A1    May 18, 2006

Related U.S. Application Data

(60) Provisional application No. 60/614,880, filed on Sep. 30, 2004.

(51) Int. Cl.
*A61B 18/04* (2006.01)
(52) U.S. Cl. ............................................. 606/34; 606/41
(58) Field of Classification Search .................... 606/32, 606/34, 41; 600/104, 131–2
See application file for complete search history.

(56) References Cited

U.S. PATENT DOCUMENTS

| | | |
|---|---|---|
| 3,266,059 A | 8/1966 | Stelle |
| 3,470,876 A | 10/1969 | Barchilon |
| 3,572,325 A | 3/1971 | Bazell et al. |
| 3,581,738 A | 6/1971 | Moore |
| 3,699,967 A * | 10/1972 | Anderson ....................... 606/37 |
| 4,108,211 A | 8/1978 | Tanaka |
| 4,261,345 A * | 4/1981 | Yamaguchi .................. 600/132 |
| 4,286,585 A | 9/1981 | Ogawa |
| 4,294,162 A | 10/1981 | Fowler et al. |

(Continued)

FOREIGN PATENT DOCUMENTS

EP    0 689 851 A1    1/1996

(Continued)

OTHER PUBLICATIONS

Invitation to Pay Additional Fees and Partial International Search Report, dated Mar. 7, 2006, for International Application No. PCT/US2005/034584, Boston Scientific Scimed, Inc., filed Sep. 29, 2005.

(Continued)

*Primary Examiner* — Michael Peffley
*Assistant Examiner* — Ronald Hupczey, Jr.
(74) *Attorney, Agent, or Firm* — Bookoff McAndrews, PLLC

(57) ABSTRACT

A multi-functional endoscopic system, for use in electrosurgical applications, that includes an imaging endoscope that may be used in combination with various electrosurgical devices, all of which are sufficiently inexpensive to manufacture, such that the endoscope and electrosurgical devices are considered single use, disposable items. The multi-functional endoscopic system of the present invention is suitable for use with a variety of common electrosurgical devices that require electrical/electronic support in order to function. The electrical/electronic support for these electrosurgical devices (e.g., an electrosurgical generator and associated controls) is integrated with the operator console of the imaging endoscope of the multi-functional endoscopic system of the present invention, rather than provided as a separate device. In another embodiment of the invention, an imaging endoscope is provided that integrates or combines the functions of both an imaging endoscope and an electrosurgical device, which can be controlled by a single handheld controller.

26 Claims, 11 Drawing Sheets

U.S. PATENT DOCUMENTS

| | | | |
|---|---|---|---|
| 4,315,309 A | 2/1982 | Coli | |
| 4,351,323 A | 9/1982 | Ouchi et al. | |
| 4,425,113 A | 1/1984 | Bilstad | |
| 4,432,349 A | 2/1984 | Oshiro | |
| 4,471,766 A | 9/1984 | Terayama | |
| 4,473,841 A | 9/1984 | Murakoshi et al. | |
| 4,487,489 A * | 12/1984 | Takamatsu | 396/17 |
| 4,488,039 A | 12/1984 | Sato et al. | |
| 4,491,865 A | 1/1985 | Danna et al. | |
| 4,495,134 A | 1/1985 | Ouchi et al. | |
| 4,499,895 A | 2/1985 | Takayama | |
| 4,513,235 A | 4/1985 | Acklam et al. | |
| 4,515,444 A | 5/1985 | Prescott et al. | |
| 4,516,063 A | 5/1985 | Kaye et al. | |
| 4,519,391 A | 5/1985 | Murakoshi | |
| 4,559,928 A | 12/1985 | Takayama | |
| 4,573,450 A | 3/1986 | Arakawa | |
| 4,580,210 A | 4/1986 | Nordstrom | |
| 4,586,923 A | 5/1986 | Gould et al. | |
| 4,601,284 A * | 7/1986 | Arakawa et al. | 600/112 |
| 4,607,621 A | 8/1986 | Wheeler | |
| 4,615,330 A | 10/1986 | Nagasaki et al. | |
| 4,616,630 A | 10/1986 | Arakawa | |
| 4,617,915 A | 10/1986 | Arakawa | |
| 4,621,618 A | 11/1986 | Omagari et al. | |
| 4,625,714 A | 12/1986 | Toyota | |
| 4,631,582 A | 12/1986 | Nagasaki et al. | |
| 4,633,303 A | 12/1986 | Nagasaki et al. | |
| 4,633,304 A | 12/1986 | Nagasaki | |
| 4,643,170 A | 2/1987 | Miyazaki et al. | |
| 4,646,723 A | 3/1987 | Arakawa | |
| 4,649,904 A | 3/1987 | Krauter et al. | |
| 4,651,202 A | 3/1987 | Arakawa | |
| 4,652,093 A | 3/1987 | Stephen et al. | |
| 4,652,916 A | 3/1987 | Suzaki et al. | |
| 4,654,701 A | 3/1987 | Yabe | |
| RE32,421 E | 5/1987 | Hattori | |
| 4,662,725 A | 5/1987 | Nisioka | |
| 4,663,657 A | 5/1987 | Nagasaki et al. | |
| 4,667,655 A | 5/1987 | Ogiu et al. | |
| 4,674,844 A | 6/1987 | Nishioka et al. | |
| 4,686,963 A | 8/1987 | Cohen et al. | |
| 4,697,210 A | 9/1987 | Toyota et al. | |
| 4,700,693 A | 10/1987 | Lia et al. | |
| 4,714,075 A | 12/1987 | Krauter et al. | |
| 4,716,457 A | 12/1987 | Matsuo | |
| 4,719,508 A | 1/1988 | Sasaki et al. | |
| 4,727,417 A | 2/1988 | Kanno et al. | |
| 4,727,418 A | 2/1988 | Kato et al. | |
| 4,745,470 A | 5/1988 | Yabe et al. | |
| 4,745,471 A | 5/1988 | Takamura et al. | |
| 4,746,974 A | 5/1988 | Matsuo | |
| 4,748,970 A | 6/1988 | Nakajima | |
| 4,755,029 A | 7/1988 | Okobe | |
| 4,762,119 A | 8/1988 | Allred et al. | |
| 4,765,312 A | 8/1988 | Sasa et al. | |
| 4,766,489 A | 8/1988 | Kato | |
| 4,787,369 A | 11/1988 | Allred et al. | |
| 4,790,294 A | 12/1988 | Allred et al. | |
| 4,794,913 A | 1/1989 | Shimonaka et al. | |
| 4,796,607 A | 1/1989 | Allred et al. | |
| 4,800,869 A | 1/1989 | Nakajima | |
| 4,805,596 A | 2/1989 | Hatori | |
| 4,806,011 A | 2/1989 | Bettinger | |
| 4,819,065 A | 4/1989 | Eino | |
| 4,819,077 A | 4/1989 | Kikuchi et al. | |
| 4,821,116 A | 4/1989 | Nagasaki et al. | |
| 4,824,225 A | 4/1989 | Nishioka | |
| 4,831,437 A | 5/1989 | Nishioka et al. | |
| 4,836,187 A | 6/1989 | Iwakoshi et al. | |
| 4,844,052 A | 7/1989 | Iwakoshi et al. | |
| 4,845,553 A | 7/1989 | Konomura et al. | |
| 4,845,555 A | 7/1989 | Yabe et al. | |
| 4,847,694 A | 7/1989 | Nishihara | |
| 4,853,772 A | 8/1989 | Kikuchi | |
| 4,860,731 A | 8/1989 | Matsuura | |
| 4,867,546 A | 9/1989 | Nishioka et al. | |
| 4,868,647 A | 9/1989 | Uehara et al. | |
| 4,869,237 A | 9/1989 | Eino et al. | |
| 4,873,965 A | 10/1989 | Danieli | |
| 4,875,468 A | 10/1989 | Krauter et al. | |
| 4,877,314 A | 10/1989 | Kanamori | |
| 4,882,623 A | 11/1989 | Uchikubo | |
| 4,884,134 A | 11/1989 | Tsuji et al. | |
| 4,885,634 A | 12/1989 | Yabe | |
| 4,890,159 A | 12/1989 | Ogiu | |
| 4,894,715 A | 1/1990 | Uchikubo et al. | |
| 4,895,431 A | 1/1990 | Tsujiuchi et al. | |
| 4,899,731 A | 2/1990 | Takayama et al. | |
| 4,899,732 A | 2/1990 | Cohen | |
| 4,899,787 A | 2/1990 | Ouchi et al. | |
| 4,905,666 A | 3/1990 | Fukuda | |
| 4,918,521 A | 4/1990 | Yabe et al. | |
| 4,919,112 A | 4/1990 | Siegmund | |
| 4,919,114 A | 4/1990 | Miyazaki | |
| 4,920,980 A | 5/1990 | Jackowski | |
| 4,928,172 A | 5/1990 | Uehara et al. | |
| 4,931,867 A | 6/1990 | Kikuchi | |
| 4,941,454 A | 7/1990 | Wood et al. | |
| 4,941,456 A | 7/1990 | Wood et al. | |
| 4,951,134 A | 8/1990 | Nakasima et al. | |
| 4,951,135 A | 8/1990 | Sasagawa et al. | |
| 4,952,040 A | 8/1990 | Igarashi | |
| 4,960,127 A | 10/1990 | Noce et al. | |
| 4,961,110 A | 10/1990 | Nakamura | |
| 4,967,269 A | 10/1990 | Sasagawa et al. | |
| 4,971,034 A | 11/1990 | Doi et al. | |
| 4,973,311 A | 11/1990 | Iwakoshi et al. | |
| 4,979,497 A | 12/1990 | Matsuura et al. | |
| 4,982,725 A | 1/1991 | Hibino et al. | |
| 4,984,878 A | 1/1991 | Miyano | |
| 4,986,642 A | 1/1991 | Yokota et al. | |
| 4,987,884 A | 1/1991 | Nishioka et al. | |
| 4,989,075 A | 1/1991 | Ito | |
| 4,989,581 A | 2/1991 | Tamburrino et al. | |
| 4,996,974 A | 3/1991 | Ciarlei | |
| 4,996,975 A | 3/1991 | Nakamura | |
| 5,001,556 A | 3/1991 | Nakamura et al. | |
| 5,005,558 A | 4/1991 | Aomori | |
| 5,005,957 A | 4/1991 | Kanamori et al. | |
| 5,007,408 A | 4/1991 | Ieoka | |
| 5,018,509 A | 5/1991 | Suzuki et al. | |
| 5,022,382 A | 6/1991 | Ohshoki et al. | |
| 5,029,016 A | 7/1991 | Hiyama et al. | |
| 5,034,888 A | 7/1991 | Uehara et al. | |
| 5,040,069 A | 8/1991 | Matsumoto et al. | |
| RE33,689 E | 9/1991 | Nishioka et al. | |
| 5,045,935 A | 9/1991 | Kikuchi | |
| 5,049,989 A | 9/1991 | Tsuji | |
| 5,050,584 A | 9/1991 | Matsuura | |
| 5,050,974 A | 9/1991 | Takasugi et al. | |
| 5,056,503 A | 10/1991 | Nagasaki | |
| 5,061,994 A | 10/1991 | Takahashi | |
| 5,068,719 A | 11/1991 | Tsuji | |
| 5,081,524 A | 1/1992 | Tsuruoka et al. | |
| 5,087,989 A | 2/1992 | Igarashi | |
| 5,110,645 A | 5/1992 | Matsumoto et al. | |
| 5,111,281 A | 5/1992 | Sekiguchi | |
| 5,111,306 A | 5/1992 | Kanno et al. | |
| 5,111,804 A | 5/1992 | Funakoshi | |
| 5,113,254 A | 5/1992 | Kanno et al. | |
| 5,119,238 A | 6/1992 | Igarashi | |
| 5,122,138 A | 6/1992 | Manwaring | |
| 5,131,393 A | 7/1992 | Ishiguro et al. | |
| 5,137,013 A | 8/1992 | Chiba et al. | |
| 5,140,265 A | 8/1992 | Sakiyama et al. | |
| 5,159,446 A | 10/1992 | Hibino et al. | |
| 5,170,775 A | 12/1992 | Tagami | |
| 5,172,225 A | 12/1992 | Takahashi et al. | |
| 5,174,293 A | 12/1992 | Hagiwara | |
| 5,176,629 A | 1/1993 | Kullas et al. | |
| 5,191,878 A | 3/1993 | Iida et al. | |
| 5,198,931 A | 3/1993 | Igarashi | |
| 5,201,908 A | 4/1993 | Jones | |
| 5,205,280 A * | 4/1993 | Dennison et al. | 600/112 |
| 5,208,702 A | 5/1993 | Shiraiwa | |
| 5,209,220 A | 5/1993 | Hiyama et al. | |

| | | | | | |
|---|---|---|---|---|---|
| 5,225,958 A | 7/1993 | Nakamura | 5,781,172 A | 7/1998 | Engel et al. |
| 5,228,356 A | 7/1993 | Chuang | 5,785,644 A | 7/1998 | Grabover et al. |
| 5,243,416 A | 9/1993 | Nakazawa | 5,788,714 A | 8/1998 | Ouchi |
| 5,243,967 A | 9/1993 | Hibino | 5,789,047 A | 8/1998 | Sasaki et al. |
| 5,257,628 A | 11/1993 | Ishiguro et al. | 5,793,539 A | 8/1998 | Konno et al. |
| 5,258,006 A | 11/1993 | Rydell et al. | 5,805,140 A | 9/1998 | Rosenberg et al. |
| 5,271,381 A | 12/1993 | Ailinger et al. | 5,810,715 A | 9/1998 | Moriyama |
| RE34,504 E | 1/1994 | Uehara et al. | 5,812,983 A | 9/1998 | Kumagai |
| 5,291,010 A | 3/1994 | Tsuji | 5,819,736 A | 10/1998 | Avny et al. |
| 5,299,559 A | 4/1994 | Bruce et al. | 5,820,591 A | 10/1998 | Thompson et al. |
| 5,311,858 A | 5/1994 | Adair | 5,821,466 A | 10/1998 | Clark et al. |
| 5,311,859 A * | 5/1994 | Monroe et al. ................ 600/112 | 5,821,920 A | 10/1998 | Rosenberg et al. |
| 5,325,845 A | 7/1994 | Adair et al. | 5,823,948 A | 10/1998 | Ross, Jr. et al. |
| 5,331,551 A | 7/1994 | Tsuruoka et al. | 5,827,186 A | 10/1998 | Chen et al. |
| 5,342,299 A | 8/1994 | Snoke et al. | 5,827,190 A | 10/1998 | Palcic et al. |
| 5,347,989 A | 9/1994 | Monroe et al. | 5,828,197 A | 10/1998 | Martin et al. |
| 5,374,953 A | 12/1994 | Sasaki et al. | 5,828,363 A | 10/1998 | Yaniger et al. |
| 5,379,757 A | 1/1995 | Hiyama et al. | 5,830,124 A | 11/1998 | Suzuki et al. |
| 5,381,782 A | 1/1995 | DeLaRama et al. | 5,830,128 A | 11/1998 | Tanaka |
| 5,390,662 A | 2/1995 | Okada | 5,836,869 A | 11/1998 | Kudo et al. |
| 5,400,769 A | 3/1995 | Tanii et al. | 5,837,023 A | 11/1998 | Koike et al. |
| 5,402,768 A | 4/1995 | Adair | 5,840,014 A | 11/1998 | Miyano et al. |
| 5,402,769 A | 4/1995 | Tsuji | 5,841,126 A | 11/1998 | Fossum et al. |
| 5,409,485 A | 4/1995 | Suda | 5,843,000 A | 12/1998 | Nishioka et al. |
| 5,412,478 A | 5/1995 | Ishihara et al. | 5,846,183 A | 12/1998 | Chilcoat |
| 5,418,649 A | 5/1995 | Igarashi | 5,855,560 A | 1/1999 | Idaomi et al. |
| 5,420,644 A | 5/1995 | Watanabe | 5,857,963 A | 1/1999 | Pelchy et al. |
| 5,431,645 A | 7/1995 | Smith et al. | 5,865,724 A | 2/1999 | Palmer et al. |
| 5,434,615 A | 7/1995 | Matsumoto | 5,868,664 A | 2/1999 | Speier et al. |
| 5,436,640 A | 7/1995 | Reeves | 5,868,666 A | 2/1999 | Okada et al. |
| 5,436,767 A | 7/1995 | Suzuki et al. | 5,873,816 A | 2/1999 | Kagawa et al. |
| 5,440,341 A | 8/1995 | Suzuki et al. | 5,873,866 A | 2/1999 | Kondo et al. |
| 5,464,007 A | 11/1995 | Krauter et al. | 5,876,326 A | 3/1999 | Takamura et al. |
| 5,469,840 A | 11/1995 | Tanii et al. | 5,876,331 A | 3/1999 | Wu et al. |
| 5,473,235 A | 12/1995 | Lance et al. | 5,876,373 A | 3/1999 | Giba et al. |
| 5,482,029 A | 1/1996 | Sekiguchi et al. | 5,876,427 A | 3/1999 | Chen et al. |
| 5,484,407 A | 1/1996 | Osypka | 5,877,819 A | 3/1999 | Branson |
| 5,485,316 A | 1/1996 | Mori et al. | 5,879,284 A | 3/1999 | Tsujita |
| 5,496,260 A | 3/1996 | Krauter et al. | 5,880,714 A | 3/1999 | Rosenberg et al. |
| 5,498,230 A * | 3/1996 | Adair ............................ 600/112 | 5,882,293 A | 3/1999 | Ouchi |
| 5,515,449 A | 5/1996 | Tsuruoka et al. | 5,882,339 A | 3/1999 | Beiser et al. |
| 5,518,501 A | 5/1996 | Oneda et al. | 5,889,670 A | 3/1999 | Schuler et al. |
| 5,543,831 A | 8/1996 | Tsuji et al. | 5,889,672 A | 3/1999 | Schuler et al. |
| 5,569,158 A | 10/1996 | Suzuki et al. | 5,892,630 A | 4/1999 | Broome |
| 5,569,159 A | 10/1996 | Anderson et al. | 5,895,350 A | 4/1999 | Hori |
| 5,586,262 A | 12/1996 | Komatsu et al. | 5,897,507 A | 4/1999 | Kortenbach et al. |
| 5,589,854 A | 12/1996 | Tsai | 5,897,525 A | 4/1999 | Dey et al. |
| 5,591,202 A | 1/1997 | Slater et al. | 5,907,487 A | 5/1999 | Rosenberg et al. |
| 5,608,451 A | 3/1997 | Konno et al. | 5,923,018 A | 7/1999 | Kameda et al. |
| 5,619,380 A | 4/1997 | Agasawa et al. | 5,928,136 A | 7/1999 | Barry |
| 5,622,528 A | 4/1997 | Hamano et al. | 5,929,607 A | 7/1999 | Rosenberg et al. |
| 5,631,695 A | 5/1997 | Nakamura et al. | 5,929,846 A | 7/1999 | Rosenberg et al. |
| 5,633,203 A | 5/1997 | Adair | 5,929,900 A | 7/1999 | Yamanaka |
| 5,643,203 A | 7/1997 | Beiser et al. | 5,929,901 A | 7/1999 | Adair et al. |
| 5,645,075 A | 7/1997 | Palmer et al. | 5,931,833 A | 8/1999 | Silverstein |
| 5,647,840 A | 7/1997 | D'Amelio et al. | 5,933,809 A | 8/1999 | Hunt et al. |
| 5,658,238 A | 8/1997 | Suzuki et al. | 5,935,085 A | 8/1999 | Welsh et al. |
| 5,667,477 A | 9/1997 | Segawa | 5,936,778 A | 8/1999 | Miyano et al. |
| 5,674,182 A | 10/1997 | Suzuki et al. | 5,941,817 A | 8/1999 | Crawford |
| 5,674,197 A | 10/1997 | van Muiden et al. | 5,950,168 A | 9/1999 | Simborg et al. |
| 5,685,823 A | 11/1997 | Ito et al. | 5,951,462 A | 9/1999 | Yamanaka |
| 5,685,825 A | 11/1997 | Takase et al. | 5,956,416 A | 9/1999 | Tsuruoka et al. |
| 5,685,877 A * | 11/1997 | Pagedas et al. .................. 606/46 | 5,956,689 A | 9/1999 | Everhart |
| 5,691,853 A | 11/1997 | Miyano | 5,956,690 A | 9/1999 | Haggerson et al. |
| 5,695,450 A | 12/1997 | Yabe et al. | 5,959,613 A | 9/1999 | Rosenberg et al. |
| 5,698,866 A | 12/1997 | Doiron et al. | 5,976,070 A | 11/1999 | Ono et al. |
| 5,702,349 A | 12/1997 | Morizumi | 5,976,074 A | 11/1999 | Moriyama |
| 5,703,724 A | 12/1997 | Miyano | 5,980,454 A | 11/1999 | Broome |
| 5,704,371 A | 1/1998 | Shepard | 5,980,468 A | 11/1999 | Zimmon |
| 5,704,896 A | 1/1998 | Fukunishi et al. | 5,986,693 A | 11/1999 | Adair et al. |
| 5,708,482 A | 1/1998 | Takahashi et al. | 5,991,729 A | 11/1999 | Barry et al. |
| 5,721,566 A | 2/1998 | Rosenberg et al. | 5,991,730 A | 11/1999 | Lubin et al. |
| 5,724,068 A | 3/1998 | Sanchez et al. | 5,999,168 A | 12/1999 | Rosenberg et al. |
| 5,728,045 A | 3/1998 | Komi | 6,002,425 A | 12/1999 | Yamanaka et al. |
| 5,739,811 A | 4/1998 | Rosenberg et al. | 6,007,531 A | 12/1999 | Snoke et al. |
| 5,740,801 A | 4/1998 | Branson | 6,014,630 A | 1/2000 | Jeacock et al. |
| 5,746,696 A | 5/1998 | Kondo | 6,015,088 A | 1/2000 | Parker et al. |
| 5,764,809 A | 6/1998 | Nomami et al. | 6,017,322 A | 1/2000 | Snoke et al. |
| 5,767,839 A | 6/1998 | Rosenberg | 6,020,875 A | 2/2000 | Moore et al. |

| | | | | | | | |
|---|---|---|---|---|---|---|---|
| 6,020,876 | A | 2/2000 | Rosenberg et al. | 6,454,162 | B1 | 9/2002 | Teller |
| 6,026,363 | A | 2/2000 | Shepard | 6,459,447 | B1 | 10/2002 | Okada et al. |
| 6,030,360 | A | 2/2000 | Biggs | 6,468,204 | B2 | 10/2002 | Sendai et al. |
| 6,032,120 | A | 2/2000 | Rock et al. | 6,475,141 | B2 | 11/2002 | Abe |
| 6,039,728 | A | 3/2000 | Berlien et al. | 6,478,730 | B1 | 11/2002 | Bala et al. |
| 6,043,839 | A | 3/2000 | Adair et al. | 6,489,987 | B1 | 12/2002 | Higuchi et al. |
| 6,050,718 | A | 4/2000 | Schena et al. | 6,496,827 | B2 | 12/2002 | Kozam et al. |
| 6,057,828 | A | 5/2000 | Rosenberg et al. | 6,498,948 | B1 | 12/2002 | Ozawa et al. |
| 6,059,719 | A | 5/2000 | Yamamoto et al. | 6,503,193 | B1 | 1/2003 | Iwasaki et al. |
| 6,061,004 | A | 5/2000 | Rosenberg | 6,520,908 | B1 | 2/2003 | Ikeda et al. |
| 6,067,077 | A | 5/2000 | Martin et al. | 6,524,234 | B2 | 2/2003 | Ouchi |
| 6,071,248 | A | 6/2000 | Zimmon | 6,530,882 | B1 | 3/2003 | Farkas et al. |
| 6,075,555 | A | 6/2000 | Street | 6,533,722 | B2 | 3/2003 | Nakashima |
| 6,078,308 | A | 6/2000 | Rosenberg et al. | 6,540,669 | B2 | 4/2003 | Abe et al. |
| 6,078,353 | A | 6/2000 | Yamanaka et al. | 6,544,194 | B1 | 4/2003 | Kortenbach et al. |
| 6,078,876 | A | 6/2000 | Rosenberg et al. | 6,545,703 | B1 | 4/2003 | Takahashi et al. |
| 6,080,104 | A | 6/2000 | Ozawa et al. | 6,551,239 | B2 | 4/2003 | Renner et al. |
| 6,081,809 | A | 6/2000 | Kumagai | 6,554,765 | B1 * | 4/2003 | Yarush et al. ................. 600/132 |
| 6,083,152 | A | 7/2000 | Strong | 6,558,317 | B2 | 5/2003 | Takahashi et al. |
| 6,083,170 | A | 7/2000 | Ben-Haim | 6,561,971 | B1 | 5/2003 | Akiba |
| 6,092,722 | A * | 7/2000 | Heinrichs et al. ............. 235/375 | 6,565,507 | B2 | 5/2003 | Kamata et al. |
| 6,095,971 | A | 8/2000 | Takahashi | 6,574,629 | B1 | 6/2003 | Cooke, Jr. et al. |
| 6,099,465 | A | 8/2000 | Inoue | 6,589,162 | B2 | 7/2003 | Nakashima et al. |
| 6,100,874 | A | 8/2000 | Schena et al. | 6,595,913 | B2 | 7/2003 | Takahashi |
| 6,104,382 | A | 8/2000 | Martin et al. | 6,597,390 | B1 | 7/2003 | Higuchi |
| 6,120,435 | A | 9/2000 | Eino | 6,599,239 | B2 | 7/2003 | Hayakawa et al. |
| 6,125,337 | A | 9/2000 | Rosenberg et al. | 6,602,186 | B1 | 8/2003 | Sugimoto et al. |
| 6,128,006 | A | 10/2000 | Rosenberg et al. | 6,605,035 | B2 | 8/2003 | Ando et al. |
| 6,132,369 | A | 10/2000 | Takahashi | 6,609,135 | B1 | 8/2003 | Omori et al. |
| 6,134,056 | A | 10/2000 | Nakamuka | 6,611,846 | B1 | 8/2003 | Stoodley |
| 6,134,506 | A | 10/2000 | Rosenberg et al. | 6,614,969 | B2 | 9/2003 | Eichelberger et al. |
| 6,135,946 | A | 10/2000 | Konen et al. | 6,616,601 | B2 | 9/2003 | Hayakawa |
| 6,139,508 | A | 10/2000 | Simpson et al. | 6,623,423 | B2 * | 9/2003 | Sakurai et al. ................. 600/104 |
| 6,141,037 | A | 10/2000 | Upton et al. | 6,623,424 | B2 | 9/2003 | Hayakawa et al. |
| 6,142,956 | A | 11/2000 | Kortenbach et al. | 6,638,214 | B2 | 10/2003 | Akiba |
| 6,146,355 | A | 11/2000 | Biggs | 6,638,215 | B2 | 10/2003 | Kobayashi |
| 6,149,607 | A | 11/2000 | Simpson et al. | 6,641,528 | B2 | 11/2003 | Torii |
| 6,152,877 | A | 11/2000 | Masters | 6,651,669 | B1 | 11/2003 | Burnside |
| 6,154,198 | A | 11/2000 | Rosenberg | 6,656,110 | B1 | 12/2003 | Irion et al. |
| 6,154,248 | A | 11/2000 | Ozawa et al. | 6,656,112 | B2 | 12/2003 | Miyanaga |
| 6,155,988 | A | 12/2000 | Peters | 6,659,940 | B2 | 12/2003 | Adler |
| 6,174,291 | B1 | 1/2001 | McMahon et al. | 6,663,561 | B2 | 12/2003 | Sugimoto et al. |
| 6,181,481 | B1 | 1/2001 | Yamamoto et al. | 6,669,629 | B2 | 12/2003 | Matsui |
| 6,184,922 | B1 | 2/2001 | Saito et al. | 6,673,012 | B2 | 1/2004 | Fujii et al. |
| 6,193,714 | B1 | 2/2001 | McGaffigan et al. | 6,677,984 | B2 | 1/2004 | Kobayashi et al. |
| 6,195,592 | B1 | 2/2001 | Schuler et al. | 6,678,397 | B1 | 1/2004 | Omori et al. |
| 6,203,493 | B1 | 3/2001 | Ben-Haim | 6,682,479 | B1 | 1/2004 | Takahashi et al. |
| 6,206,824 | B1 | 3/2001 | Ohara et al. | 6,685,631 | B2 | 2/2004 | Minami |
| 6,211,904 | B1 | 4/2001 | Adair | 6,686,949 | B2 | 2/2004 | Kobayashi et al. |
| 6,216,104 | B1 | 4/2001 | Moshfeghi et al. | 6,690,409 | B1 | 2/2004 | Takahashi |
| 6,219,091 | B1 | 4/2001 | Yamanaka et al. | 6,690,963 | B2 | 2/2004 | Ben-Haim et al. |
| 6,221,070 | B1 | 4/2001 | Tu et al. | 6,692,431 | B2 | 2/2004 | Kazakevich |
| 6,231,572 | B1 | 5/2001 | Hart et al. | 6,697,101 | B1 | 2/2004 | Takahashi et al. |
| 6,241,668 | B1 | 6/2001 | Herzog | 6,699,181 | B2 | 3/2004 | Wako |
| 6,260,994 | B1 | 7/2001 | Matsumoto et al. | 6,702,737 | B2 | 3/2004 | Hinto et al. |
| 6,272,470 | B1 | 8/2001 | Teshima | 6,711,426 | B2 | 3/2004 | Benaron et al. |
| 6,275,255 | B1 | 8/2001 | Adair et al. | 6,715,068 | B2 | 3/2004 | Abe |
| 6,283,960 | B1 | 9/2001 | Ashley | 6,716,162 | B2 | 4/2004 | Hakamata |
| 6,295,082 | B1 | 9/2001 | Dowdy et al. | 6,728,599 | B2 | 4/2004 | Wang et al. |
| 6,299,625 | B1 | 10/2001 | Bacher | 6,730,018 | B2 | 5/2004 | Takase |
| 6,309,347 | B1 | 10/2001 | Takahashi et al. | 6,736,773 | B2 | 5/2004 | Wendlandt et al. |
| 6,310,642 | B1 | 10/2001 | Adair et al. | 6,743,240 | B2 | 6/2004 | Smith et al. |
| 6,319,196 | B1 | 11/2001 | Minami | 6,749,559 | B1 | 6/2004 | Kraas et al. |
| 6,319,197 | B1 | 11/2001 | Tsuji et al. | 6,749,560 | B1 | 6/2004 | Konstorum et al. |
| 6,322,494 | B1 | 11/2001 | Bullivant et al. | 6,749,561 | B2 | 6/2004 | Kazakevich |
| 6,334,844 | B1 | 1/2002 | Akiba | 6,753,905 | B1 | 6/2004 | Okada et al. |
| 6,346,075 | B1 | 2/2002 | Arai et al. | 6,758,806 | B2 | 7/2004 | Kamrava et al. |
| 6,366,799 | B1 | 4/2002 | Acker et al. | 6,758,807 | B2 | 7/2004 | Minami |
| 6,381,029 | B1 | 4/2002 | Tipirneni | 6,758,842 | B2 | 7/2004 | Irion et al. |
| 6,398,724 | B1 | 6/2002 | May et al. | 6,778,208 | B2 | 8/2004 | Takeshige et al. |
| 6,413,207 | B1 | 7/2002 | Minami | 6,780,151 | B2 | 8/2004 | Grabover et al. |
| 6,421,078 | B1 | 7/2002 | Akai et al. | 6,785,410 | B2 | 8/2004 | Vining et al. |
| 6,425,535 | B1 | 7/2002 | Akiba | 6,785,593 | B2 | 8/2004 | Wang et al. |
| 6,425,858 | B1 | 7/2002 | Minami | 6,796,938 | B2 | 9/2004 | Sendai |
| 6,436,032 | B1 | 8/2002 | Eto et al. | 6,796,939 | B1 | 9/2004 | Konomura et al. |
| 6,441,845 | B1 | 8/2002 | Matsumoto | 6,798,533 | B2 | 9/2004 | Tipirneni |
| 6,447,444 | B1 | 9/2002 | Avni et al. | 6,800,056 | B2 | 10/2004 | Tartaglia et al. |
| 6,449,006 | B1 | 9/2002 | Shipp | 6,800,057 | B2 | 10/2004 | Tsujita et al. |
| 6,453,190 | B1 | 9/2002 | Acker et al. | 6,808,491 | B2 | 10/2004 | Kortenbach et al. |

| | | | |
|---|---|---|---|
| 6,824,539 B2 | 11/2004 | Novak | |
| 6,824,548 B2 | 11/2004 | Smith et al. | |
| 6,829,003 B2 | 12/2004 | Takami | |
| 6,830,545 B2 | 12/2004 | Bendall | |
| 6,832,990 B2 | 12/2004 | Kortenbach et al. | |
| 6,840,932 B2 | 1/2005 | Lang et al. | |
| 6,842,196 B1 | 1/2005 | Swift et al. | |
| 6,846,286 B2 | 1/2005 | Hashiyama et al. | |
| 6,847,933 B1 | 1/2005 | Hastings | |
| 6,849,043 B2 | 2/2005 | Kondo | |
| 6,850,794 B2 | 2/2005 | Shahidi | |
| 6,855,109 B2 | 2/2005 | Obata et al. | |
| 6,858,004 B1 | 2/2005 | Ozawa et al. | |
| 6,858,014 B2 | 2/2005 | Damarati | |
| 6,860,849 B2 | 3/2005 | Matsushita et al. | |
| 6,863,650 B1 | 3/2005 | Irion | |
| 6,863,661 B2 | 3/2005 | Carrillo et al. | |
| 6,868,195 B2 | 3/2005 | Fujita | |
| 6,871,086 B2 | 3/2005 | Nevo et al. | |
| 6,873,352 B2 | 3/2005 | Mochida et al. | |
| 6,876,380 B2 | 4/2005 | Abe et al. | |
| 6,879,339 B2 | 4/2005 | Ozawa | |
| 6,881,188 B2 | 4/2005 | Furuya et al. | |
| 6,882,785 B2 | 4/2005 | Eichelberger et al. | |
| 6,887,195 B1 | 5/2005 | Pilvisto | |
| 6,890,294 B2 | 5/2005 | Niwa et al. | |
| 6,892,090 B2 | 5/2005 | Verard et al. | |
| 6,892,112 B2 | 5/2005 | Wang et al. | |
| 6,895,268 B1 | 5/2005 | Rahn et al. | |
| 6,898,086 B2 | 5/2005 | Takami et al. | |
| 6,899,673 B2 | 5/2005 | Ogura et al. | |
| 6,899,674 B2 | 5/2005 | Viebach et al. | |
| 6,899,705 B2 | 5/2005 | Niemeyer | |
| 6,900,829 B1 | 5/2005 | Ozawa et al. | |
| 6,902,527 B1 | 6/2005 | Doguchi et al. | |
| 6,902,529 B2 | 6/2005 | Onishi et al. | |
| 6,903,761 B1 | 6/2005 | Abe et al. | |
| 6,903,883 B2 | 6/2005 | Amanai | |
| 6,905,057 B2 | 6/2005 | Swayze et al. | |
| 6,905,462 B1 | 6/2005 | Homma | |
| 6,908,427 B2 | 6/2005 | Fleener et al. | |
| 6,908,429 B2 | 6/2005 | Heimberger et al. | |
| 6,911,916 B1 | 6/2005 | Wang et al. | |
| 6,916,286 B2 | 7/2005 | Kazakevich | |
| 6,923,818 B2 | 8/2005 | Muramatsu et al. | |
| 6,928,490 B1 | 8/2005 | Bucholz et al. | |
| 6,930,706 B2 | 8/2005 | Kobayashi et al. | |
| 6,932,761 B2 | 8/2005 | Maeda et al. | |
| 6,934,093 B2 | 8/2005 | Kislev et al. | |
| 6,934,575 B2 | 8/2005 | Ferre et al. | |
| 6,943,663 B2 | 9/2005 | Wang et al. | |
| 6,943,946 B2 | 9/2005 | Fiete | |
| 6,943,959 B2 | 9/2005 | Homma | |
| 6,943,966 B2 | 9/2005 | Konno | |
| 6,944,031 B2 | 9/2005 | Takami et al. | |
| 6,949,068 B2 | 9/2005 | Taniguchi et al. | |
| 6,950,691 B2 | 9/2005 | Uchikubo | |
| 6,955,671 B2 | 10/2005 | Uchikubo | |
| 7,214,183 B2 * | 5/2007 | Miyake | 600/131 |
| 2001/0039370 A1 | 11/2001 | Takahashi et al. | |
| 2001/0049491 A1 | 12/2001 | Shimada | |
| 2002/0017515 A1 | 2/2002 | Obata et al. | |
| 2002/0028984 A1 | 3/2002 | Hayakawa et al. | |
| 2002/0055669 A1 | 5/2002 | Konno | |
| 2002/0080248 A1 | 6/2002 | Adair et al. | |
| 2002/0087048 A1 | 7/2002 | Brock et al. | |
| 2002/0087166 A1 | 7/2002 | Brock et al. | |
| 2002/0095175 A1 | 7/2002 | Brock et al. | |
| 2002/0128633 A1 | 9/2002 | Brock et al. | |
| 2002/0177847 A1 * | 11/2002 | Long | 606/46 |
| 2002/0193664 A1 | 12/2002 | Ross et al. | |
| 2003/0032863 A1 | 2/2003 | Kazakevich | |
| 2003/0069897 A1 | 4/2003 | Roy et al. | |
| 2003/0149338 A1 | 8/2003 | Francois et al. | |
| 2003/0176880 A1 * | 9/2003 | Long et al. | 606/167 |
| 2003/0181900 A1 * | 9/2003 | Long | 606/41 |
| 2003/0181905 A1 | 9/2003 | Long | |
| 2004/0030333 A1 | 2/2004 | Goble | |
| 2004/0049097 A1 | 3/2004 | Miyake | |
| 2004/0054258 A1 | 3/2004 | Maeda et al. | |
| 2004/0073083 A1 | 4/2004 | Ikeda et al. | |
| 2004/0073084 A1 | 4/2004 | Maeda et al. | |
| 2004/0073085 A1 | 4/2004 | Ikeda et al. | |
| 2004/0111012 A1 | 6/2004 | Whitman | |
| 2004/0147809 A1 | 7/2004 | Kazakevich | |
| 2004/0167379 A1 | 8/2004 | Akiba | |
| 2004/0249247 A1 | 12/2004 | Iddan | |
| 2004/0257608 A1 | 12/2004 | Tipirneni | |
| 2004/0267297 A1 * | 12/2004 | Malackowski | 606/167 |
| 2005/0197861 A1 | 9/2005 | Omori et al. | |
| 2005/0203341 A1 | 9/2005 | Welker et al. | |
| 2005/0228697 A1 | 10/2005 | Funahashi | |
| 2006/0052663 A1 * | 3/2006 | Koitabashi | 600/132 |
| 2008/0140158 A1 * | 6/2008 | Hamel et al. | 607/60 |

FOREIGN PATENT DOCUMENTS

| | | |
|---|---|---|
| EP | 0 834 290 A2 * | 4/1998 |
| EP | 1 300 883 A2 | 4/2003 |
| EP | 1 402 837 A | 3/2004 |
| GB | 661997 * | 5/1949 |
| GB | 661 997 A | 11/1951 |
| JP | 57-067701 | 4/1982 |
| JP | 58-78635 A | 5/1983 |
| JP | 05-31071 A | 2/1993 |
| JP | 05-091972 A | 4/1993 |
| JP | 06-105800 A | 4/1994 |
| JP | 3372273 B2 | 4/1994 |
| JP | 06-254048 A | 9/1994 |
| JP | 3219521 B2 | 9/1994 |
| JP | 07-8441 A | 1/1995 |
| JP | 3482238 B2 | 12/1995 |
| JP | 10-113330 A | 5/1998 |
| JP | 10-286221 A | 10/1998 |
| JP | 11-056777 | 3/1999 |
| JP | 11-216113 A | 8/1999 |
| JP | 2000-166928 | 6/2000 |
| JP | 2002-102152 A | 4/2002 |
| JP | 2002-177197 A | 6/2002 |
| JP | 2002-185873 A | 6/2002 |
| JP | 2002-253481 A | 9/2002 |
| JP | 2003-75113 A | 3/2003 |
| JP | 2004-130126 | 4/2004 |
| JP | 2005-342401 | 12/2005 |
| JP | 2006-057195 | 3/2006 |
| JP | 2009-238924 | 10/2009 |
| WO | WO 93/13704 A1 | 7/1993 |
| WO | WO 00/74556 A | 12/2000 |
| WO | WO 03/049630 A | 6/2003 |
| WO | WO 2004/016310 A2 | 2/2004 |
| WO | WO 2004/030526 | 4/2004 |
| WO | WO 2005/023082 A2 | 3/2005 |

OTHER PUBLICATIONS

Office Action for Japanese Patent Application No. 2007-534707, Mar. 24, 2011, 7 pages.

* cited by examiner

MULTI-FUNCTIONAL ENDOSCOPIC SYSTEM FOR USE IN ELECTROSURGICAL APPLICATIONS

CROSS-REFERENCE TO RELATED APPLICATION

The present application claims the benefit of U.S. Provisional Application No. 60/614,880, filed Sep. 30, 2004.

FIELD OF THE INVENTION

The present invention relates to medical devices, in general, and therapeutic and diagnostic endoscopes, in particular.

BACKGROUND OF THE INVENTION

As an aid to the early detection and treatment of disease, it has become well established that there are major public health benefits that result from regular endoscopic examination and subsequent or simultaneous treatment of internal structures, such as the alimentary canals and airways, e.g., the esophagus, stomach, lungs, colon, uterus, ureter, kidney and other organ systems. A conventional imaging endoscope used for such procedures is formed of a flexible tube that has a fiber optic light guide that directs illuminating light from an external light source to the distal tip, where it exits the endoscope and illuminates the tissue to be examined. Frequently, additional optical components are incorporated, in order to adjust the spread of light exiting the fiber bundle at the distal tip. An objective lens and fiber optic imaging light guide communicating with a camera at the proximal end of the endoscope or an imaging camera chip installed at the distal tip produces an image that is displayed to the examiner. In addition, most endoscopes include one or more working channels, through which medical devices, such as biopsy forceps, snares, fulguration probes, and other tools, may be passed.

Navigating the endoscope through complex and tortuous paths in a way that produces minimum pain, side effects, risk, or sedation to the patient is critical to the success of the examination. To this end, modern endoscopes include means for deflecting the distal tip of the endoscope to follow the pathway of the structure under examination, with minimum deflection or friction force upon the surrounding tissue. By manipulating a set of control knobs, the examiner is able to steer the endoscope during insertion and direct it to a region of interest, in spite of the limitations of such traditional control systems, which may be clumsy, non-intuitive, and friction-limited.

In some endoscopic procedures, it is desirable to pass an electrosurgical instrument through a working channel. The electrosurgical instruments are typically separate devices that are connected to a separate radio frequency (RF) generator source, i.e., electrosurgical generator, which is separate from the operator console of the endoscope. For example, a polypectomy snare is one such electrosurgical device that is used to perform a polypectomy procedure. A polypectomy procedure requires many steps that include, for example, the user's navigating the endoscope shaft through the colon, identifying the polyp to be removed, selecting a polypectomy snare of appropriate size, connecting the cable of the polypectomy snare to a separate electrosurgical generator, selecting the power level of the electrosurgical generator, positioning an activation foot pedal that is attached to the generator near the user, passing the polypectomy snare through the working channel, capturing the polyp in the snare, energizing the polypectomy snare with the foot pedal while viewing on a video display of the endoscope operator console, cutting off the polyp, de-energizing the polypectomy snare by removing pressure on the foot pedal, withdrawing the polypectomy snare from the working channel, and recovering the polyp through the working channel, either by suction or via another instrument.

The above-described process is very labor- and time-intensive, and the cost of the separate electrosurgical instrumentation, in combination with the endoscope system, is high and, thus, adds cost to the medical procedure. Many connections and settings have to be managed by the physician or assistant. For example, the physician cannot watch the video display of the endoscope operator console, while at the same time adjusting the settings of the electrosurgical generator, which is typically located behind the physician. Therefore, instructions are given to a nurse, for example, if the generator settings need adjustment. Overall, the system setup may be disadvantageous, in that there may be many electrical cords required in order to interconnect all the instrumentation that is typically set up in a small space, which may contribute to a less-than-safe working environment. Additionally, the foot pedal to energize the electrosurgical instrument is often awkward for the physician to locate and use. Furthermore, because the endoscope and the electrosurgical generator do not have a common user interface, the physician must familiarize himself/herself with the user interface of the endoscope as well as the user interface of all the different electrosurgical devices.

To overcome these and other problems, there is a need for a low-cost imaging endoscope and associated electrosurgical devices that can be used for a single procedure and thrown away. The endoscopic system should have improved simplicity and ease of use, a common user interface for the endoscope and associated electrosurgical devices, increased efficiency, greater clinical productivity and patient throughput, improved safety, and improved clinical advantages, by being able to do more than one task and, thus, fewer insertions, which has the result of requiring less medication and facilitating faster recovery for the patient. Additionally, it would be beneficial to provide an endoscopic system that has an improved data gathering and management system, i.e., fast and accurate electronic recording of all aspects of each procedure.

SUMMARY OF THE INVENTION

To achieve the above and other objects, in accordance with one embodiment of the present invention, a multi-functional endoscopic system is provided for use in electrosurgical applications. The system includes generally four elements: an imaging endoscope, an operator console coupled with the imaging endoscope, at least one electrosurgical device coupled with the imaging endoscope, and an electrical/electronic support for the at least one electrosurgical device (e.g., an electrosurgical generator and associated controls), which is integrated into the operator console. Thus, the electrical/electronic support for the at least one electrosurgical device is integrally provided in the operator console for the imaging endoscope, rather than provided as a separate device.

In accordance with another embodiment of the present invention, the imaging endoscope and/or the at least one electrosurgical device are configured to be disposable after a single use.

In accordance with another embodiment of the present invention, the at least one electrosurgical device may be any one of a biopsy device, a snare device, a Tomes cutter, an injection device, a probe device, a needle knife device, a spatula device (for wide area ablation), a basket device, an ultrasonic device, an RF device, and an argon plasma ablation device.

In accordance with yet another embodiment of the present invention, the at least one electrosurgical device may include an optical memory or an RFID tag containing its type (e.g., ID) information, and the operator console may include means for reading the type information so as to retrieve settings corresponding to the identified electrosurgical device as stored in the operator console memory.

In accordance with a further embodiment of the present invention, the imaging endoscope and the at least one electrosurgical device are integrally formed.

In accordance with still another embodiment of the present invention, the imaging endoscope includes at least one working channel through which the at least one electrosurgical device is inserted.

In accordance with another embodiment of the present invention, the multi-functional endoscopic system further includes a video display coupled to the operator console. The video display is configured to provide a graphical representation that is specific to the at least one electrosurgical device, after the operator console determines the type of the at least one electrosurgical device.

In accordance with another embodiment of the present invention, the imaging endoscope includes a handheld controller, which is coupled to the operator console. The handheld controller is configured to control the operation of not only the imaging endoscope but also the at least one electrosurgical device. In a further aspect of the present invention, the at least one electrosurgical device is coupled to the imaging endoscope at the handheld controller. In a still further aspect of the present invention, the handheld controller is configured to permit a user to selectively activate the electrical/electronic support for the at least one electrosurgical device.

In accordance with yet another embodiment of the present invention, a multi-functional endoscopic system is provided for use in surgical applications, which includes generally four elements: an imaging endoscope, an operator console coupled with the imaging endoscope, a handheld controller coupled with the operator console, and at least one surgical device coupled with the handheld controller. The handheld controller is configured to control the operation of not only the imaging endoscope but also the at least one surgical device.

In accordance with another embodiment of the present invention, a multi-functional endoscopic system for use in surgical applications is provided. The system includes: an imaging endoscope; a handheld controller coupled to the imaging endoscope; and at least one surgical device integrally formed with the imaging endoscope. The at least one surgical device is coupled to the handheld controller. The handheld controller is configured to control the operation of the imaging endoscope and the at least one surgical device.

In accordance with a further embodiment of the present invention, an operator console for an imaging endoscope is provided. The console integrally includes an electrical/electronic support for at least one electrosurgical device. In one embodiment, the electrical/electronic support is an electrosurgical generator for the at least one electrosurgical device.

In accordance with yet another embodiment of the present invention, a multi-functional electrosurgical system is provided. The system includes at least one electrosurgical device, and an operator console having an electrical/electronic support for the at least one electrosurgical device. Each of the at least one electrosurgical device includes a smart device, such as an RFID tag, containing information directed to a type and perhaps also working parameters of the electrical device. The operator console is configured to determine the type (and perhaps also the working parameters) of the at least one electrosurgical device based on the smart card so as to operate the electrical/electronic support based on the determination.

BRIEF DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein.

DETAILED DESCRIPTION OF THE PREFERRED EMBODIMENT

The present invention is a multi-functional endoscopic system for use in electrosurgical applications. The multi-functional endoscopic system includes an imaging endoscope that may be used in combination with various electrosurgical devices, all of which are sufficiently inexpensive to manufacture, such that the endoscope and electrosurgical devices are considered single use, disposable items. The multi-functional endoscopic system of the present invention is suitable for use with a variety of common electrosurgical devices that are used, typically, in combination with an imaging endoscope and that require electrical/electronic support to function. The electrical/electronic support for these electrosurgical devices (e.g., an electrosurgical generator and associated controls) may be integrated into an operator console of the imaging endoscope of the multi-functional endoscopic system of the present invention, rather than provided as a separate device, as is the case in typical endoscopic systems. In another embodiment of the invention, an integrated imaging endoscope is provided that integrates, into one apparatus, the functions of both an imaging endoscope and an electrosurgical device. The integrated imaging endoscope is sufficiently inexpensive to manufacture, such that it is considered a single use, disposable item.

Figure 1:
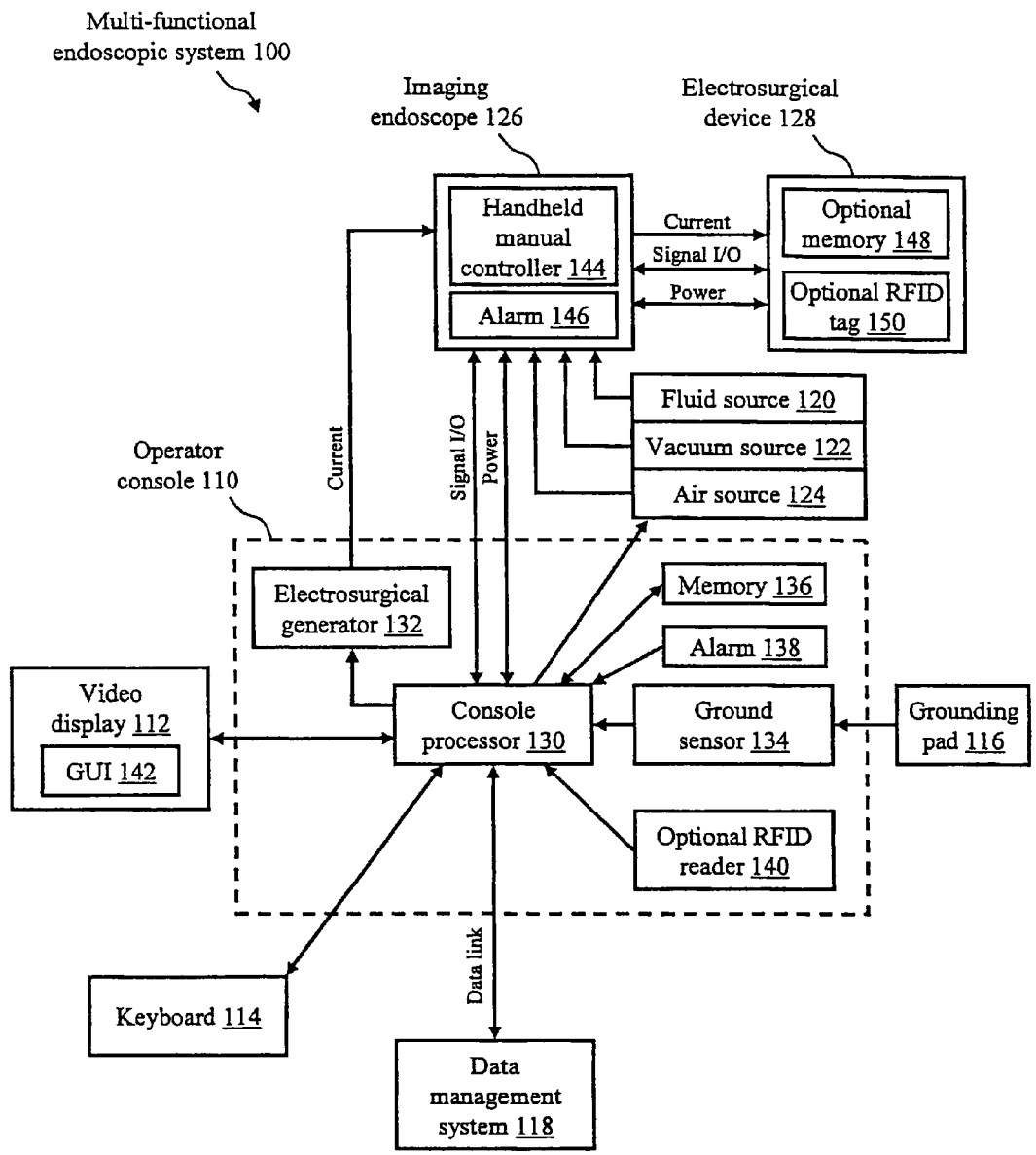
FIG. 1 illustrates a functional block diagram of a multi-functional endoscopic system for use in electrosurgical applications in accordance with an embodiment of the invention.

FIG. 1 illustrates a functional block diagram of an exemplary multifunctional endoscopic system 100 for use in electrosurgical applications in accordance with one embodiment of the invention. Multifunctional endoscopic system 100 includes an operator console 110 that is electrically connected to a video display 112, a keyboard 114, a grounding pad 116, and a data management system 118. Multi-functional endoscopic system 100 further includes a fluid source 120, a vacuum source 122, an air source 124, and a single-use imaging endoscope 126 that are all electrically, mechanically, and fluidly connected to operator console 110, and an electrosurgical device 128 that is electrically, mechanically, and fluidly connected to imaging endoscope 126.

Operator console 110 further includes a console processor 130, an electrosurgical generator 132, a ground sensor 134, a memory 136, an alarm 138, and an optional radio frequency identification (RFID) reader 140. Video display 112 further includes a graphical user interface (GUI) 142, which may include a touch screen for receiving user input. Imaging endoscope 126 further includes a handheld manual controller 144 and an alarm 146. Electrosurgical device 128 further includes an optional memory 148 and an optional RFID tag 150. Additional details of operator console 110, imaging endoscope 126, electrosurgical device 128, and handheld manual controller 144 are found in reference to FIGS. 2 through 6.

Operator console 110 is described generally as a special-purpose electronic and electromechanical apparatus that facilitates, processes, and manages all functions of multifunctional endoscopic system 100 via console processor 130, which is representative of a standard microprocessor device, such as a Philips 8051 8-bit microcontroller or a Motorola 6816 16-bit microcontroller. Console processor 130 is loaded with software for managing, for example, the operation of imaging endoscope 126 and its associated imaging electronics (not shown) to create and/or transfer images received from an image sensor within imaging endoscope 126 to video display 112 for viewing by a user, the operation of electrosurgical device 128, the operation of electrosurgical generator 132, and data transfer to and from data management system 118.

Additionally, operator console 110 includes a physical connection to imaging endoscope 126, a network connection to remote data management system 118, and connections to fluid source 120, vacuum source 122, and air source 124, which are representative of sources of air, vacuum, insufflation gas, and/or fluids. Fluids include, for example, irrigation liquids, medication, and dyes for marking tissue.

Video display 112 and keyboard 114 are standard I/O devices used with computers and the like. Video display 112 is any special-purpose or conventional computer display device, such as a computer monitor or flat panel display, which outputs graphical images to a user, for example, via GUI 142, which provides a system- or instrument-specific graphical representation of the various functions of multifunctional endoscopic system 100. Additionally, GUI 142 of video display 112 may be configured to include a touch screen for receiving user input.

Electrosurgical generator 132 is representative of a commercially available or custom designed device used in electrosurgery, wherein radiofrequency energy is used to produce cutting and/or coagulation in body tissues. More specifically, electrosurgical generator 132 is a machine that coverts low-frequency alternating current to high-frequency electrosurgical current, i.e., radiofrequency energy. Electrosurgical generator 132 is capable of providing high-frequency electrosurgical current to electrosurgical device 128. Electrosurgical generator 132 is integrated physically into the apparatus of operator console 110, rather than provided as a separate device, as is the case in typical endoscopic systems.

Ground sensor 134 is used to sense whether grounding pad 116 is properly attached to the patient. Grounding pad 116 and ground sensor 134 are required in the case in which electrosurgical device 128 is a monopolar device and are not used in the case in which electrosurgical device 128 is a bipolar device. A monopolar electrosurgical device is one wherein the active electrode of the device requires the use of a dispersive pad, i.e., grounding pad 116, to complete the circuit. By contrast, a bipolar electrosurgical device is one wherein the device has both active and return electrodes in one handpiece. Monopolar vs. bipolar instrumentation is procedure dependant.

Memory 136 is any commercially available non-volatile, writable/readable computer memory device, such as any standard FLASH memory device. The write/read operations of memory 136 are controlled via console processor 130. Memory 136 serves as local storage for information that, subsequently, may be transferred to/from data management system 118 or displayed to the user. Types of information that are stored in memory 136 are, for example, user information, user preferences, type of and default settings of attached electrosurgical device, and electrosurgical generator 132 settings, such as the energy level and duration of the current. The information stored in memory 136 may be transmitted to data management system 118 and used, for example, for performing any desired tracking operations or for generating procedure reports. Data management system 118 is representative of a centralized repository that is networked by any standard wired or wireless data link to one or more multi-functional endoscopic systems 100.

Alarm 138 of operator console 110 and alarm 146 of imaging endoscope 126 are representative of any standard, audible and/or visible alarm mechanism, such as an audio speaker and/or a light source. Conditions that may trigger alarm 138 and alarm 146 are, for example, ground sensor 134 sensing that grounding pad 116 is not properly attached to the patient or the electrical or mechanical connections to fluid source 120, vacuum source 122, air source 124, imaging endoscope 126, or electrosurgical device 128 being not properly connected. A visual alarm indication may also be provided by GUI 142 via video display 112.

Imaging endoscope 126 is an instrument that allows for the examination of the interior of a canal or hollow organ of a patient. Imaging endoscope 126 further includes an illumination mechanism (not shown), an image sensor (not shown), and an elongate shaft (not shown) that has one or more lumens located therein. Imaging endoscope 126 may be designed to be sufficiently inexpensive to manufacture, such that it may be considered a single use, disposable item, such as is described in reference to U.S. patent application Ser. Nos. 10/811,781, filed Mar. 29, 2004, 10/406,149, filed Apr. 1, 2003, and 10/956,007, filed Sep. 30, 2004, assigned to Scimed Life Systems, Inc., now Boston Scientific Scimed, Inc. and which are incorporated herein by reference. The '007 patent application describes an endoscope imaging system that includes a reusable control cabinet with a number of actuators, or a manual control on the endoscope, that controls the orientation of a lightweight endoscope. The endoscope may be used with a single patient and then disposed. The endoscope includes an illumination mechanism, an image sensor, and an elongate shaft that has one or more lumens located therein. An articulation joint at the distal end of the endoscope allows the distal end to be oriented by the actuators in the control cabinet. Further details of imaging endoscope 126 are found in reference to FIGS. 2 through 6.

Handheld manual controller 144 of imaging endoscope 126 is a handheld device that is electrically and mechanically connected to operator console 110. Handheld manual controller 144 accepts inputs from a human operator via standard push buttons, rotary knobs, joysticks, or other activation devices either singularly or in combination to control the operation of imaging endoscope 126 and electrosurgical device 128. Handheld manual controller 144 of imaging endoscope 126 provides a direct electrical connection port for connecting electrosurgical device 128 to operator console 110 and, subsequently, to electrosurgical generator 132. Further details of handheld manual controller 144 are found in reference to FIGS. 2 through 6.

Electrosurgical device 128 is representative of a variety of common or to-be-developed electrosurgical medical devices used in combination with an endoscope, for example but not limited to, a biopsy device, a snare device, a Tomes cutter, an injection device, a probe device, a needle knife device, a spatula device (for wide area ablation), a basket device, an ultrasonic device, an RF device, and an argon plasma ablation device (which would require an argon source). These devices require electrical/electronic support in order to function in endoscopes. The electrical/electronic support for electrosurgical device 128 (i.e., electrosurgical generator 132 and associated controls) is integrated into operator console 110 of multi-functional endoscopic system 100, rather than provided as a separate device, as is the case in typical endoscopic systems. Either optional memory 148 or optional RFID tag 150 may be installed in electrosurgical device 128 as a means to provide device information, such as device type identification and the associated default operation settings. In the case of optional memory 148, which is, for example, any commercially available, non-volatile read-only memory (ROM), this information is transmitted directly to and processed by console processor 130. In the case of optional RFID tag 150, a user must swipe electrosurgical device 128 in close proximity to optional RFID reader 140 of operator console 110 and, thus, the information is extracted and then processed by console processor 130. Like imaging endoscope 126, electrosurgical device 128 is sufficiently inexpensive to manufacture, such that it is considered a single use, disposable item. Further details of electrosurgical device 128 are found in reference to FIGS. 4 through 6.

Optional RFID reader 140 of operator console 110 is used in combination with optional RFID tag 150 of electrosurgical device 128. Optional RFID tag 150 is a well-known electronic product code (EPC) device that provides a unique, factory-programmed identification code. Optional RFID tag 150 is, for example, a low frequency, battery-free transponder device that is read via radio waves. An example of optional RFID tag 150 is an RFID tag manufactured by Texas Instruments Inc (Dallas, Tex.). Typically, up to 96 bits of information are stored upon an RFID tag. These 96 bits provide product information, such as product name, product manufacturer, and a 40-bit serial number. Optional RFID tag 150 may be a read-only device or a read/write device that can be programmed. The factory-programmed identification code (e.g., EPC) upon optional RFID tag 150 may be extracted via optional RFID reader 140, which is located within operator console 110. Optional RFID reader 140 is an electronic device formed of an RF transmitter and receiver and an antenna to communicate with RFID transponders, such as optional RFID tag 150. Optional RFID reader 140 is a device that scans optional RFID tag 150 via radio waves and passes the information in digital form to memory 136 or data management system 118 via console processor 130. Example manufacturers of RFID readers include Antenova Ltd. (Cambridge, England) and Bancolini (Bologna, Italy).

Figure 2:
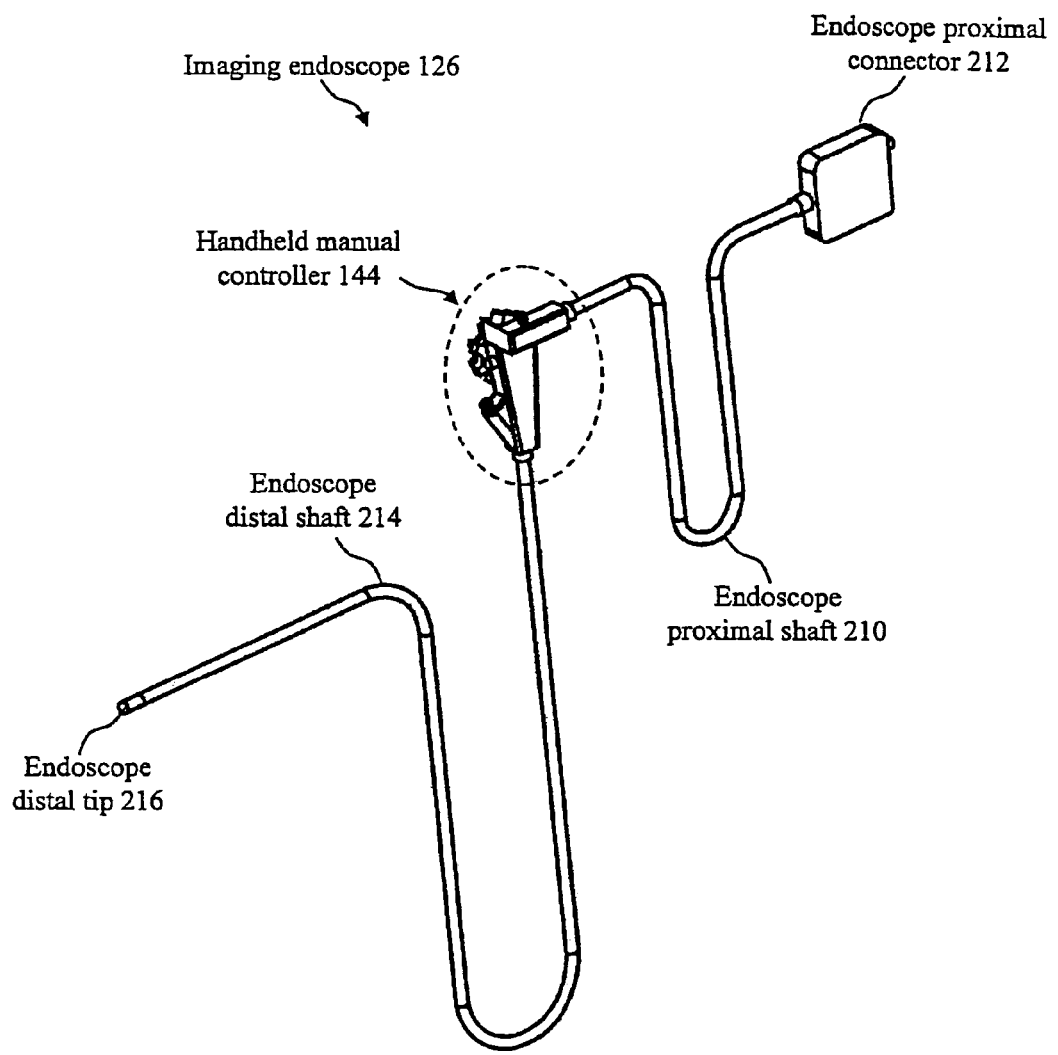
FIG. 2 illustrates a perspective view of an imaging endoscope in accordance with a first embodiment of the invention.

FIG. 2 illustrates a perspective view of imaging endoscope 126 in accordance with a first embodiment of the invention. FIG. 2 shows that imaging endoscope 126 includes an endoscope proximal shaft 210 that is electrically, mechanically, and fluidly connected, at one end, to an endoscope proximal connector 212 and, at an opposite end, to a port of handheld manual controller 144. Imaging endoscope 126 further includes an endoscope distal shaft 214 that is electrically, mechanically, and fluidly connected, at one end, to a port of handheld manual controller 144, which is further detailed in reference to FIG. 3, and has an endoscope distal tip 216 located as its opposite end for advancing into a patient's body.

The housing of endoscope proximal connector 212 is formed of a suitably lightweight, rigid material, such as molded plastic. Endoscope proximal connector 212 provides a quick-release mechanism for making and breaking all electrical, mechanical, and fluid/air/vacuum connections. The quick-release mechanism allows endoscope proximal connector 212 to be easily secured to the exterior of operator console 110. Endoscope proximal connector 212 includes wires and tubes (not shown) that pass through endoscope proximal shaft 210, then through handheld manual controller 144, then through endoscope distal shaft 214 and then to endoscope distal tip 216.

Endoscope proximal shaft 210 and endoscope distal shaft 214 are formed of a suitably lightweight, flexible material, such as polyurethane. Endoscope proximal shaft 210 and endoscope distal shaft 214 are elongated shafts that have one or more lumens located therein and wiring located therein to support, for example, a working channel, a bolus wash, jet wash, or lens wash mechanism, and an illumination mechanism and an image sensor that are located at endoscope distal tip 216. Also included within handheld manual controller 144 and endoscope distal shaft 214 are the electrical and mechanical mechanisms for articulating endoscope distal tip 216 for advancing into a patient.

Figure 3:
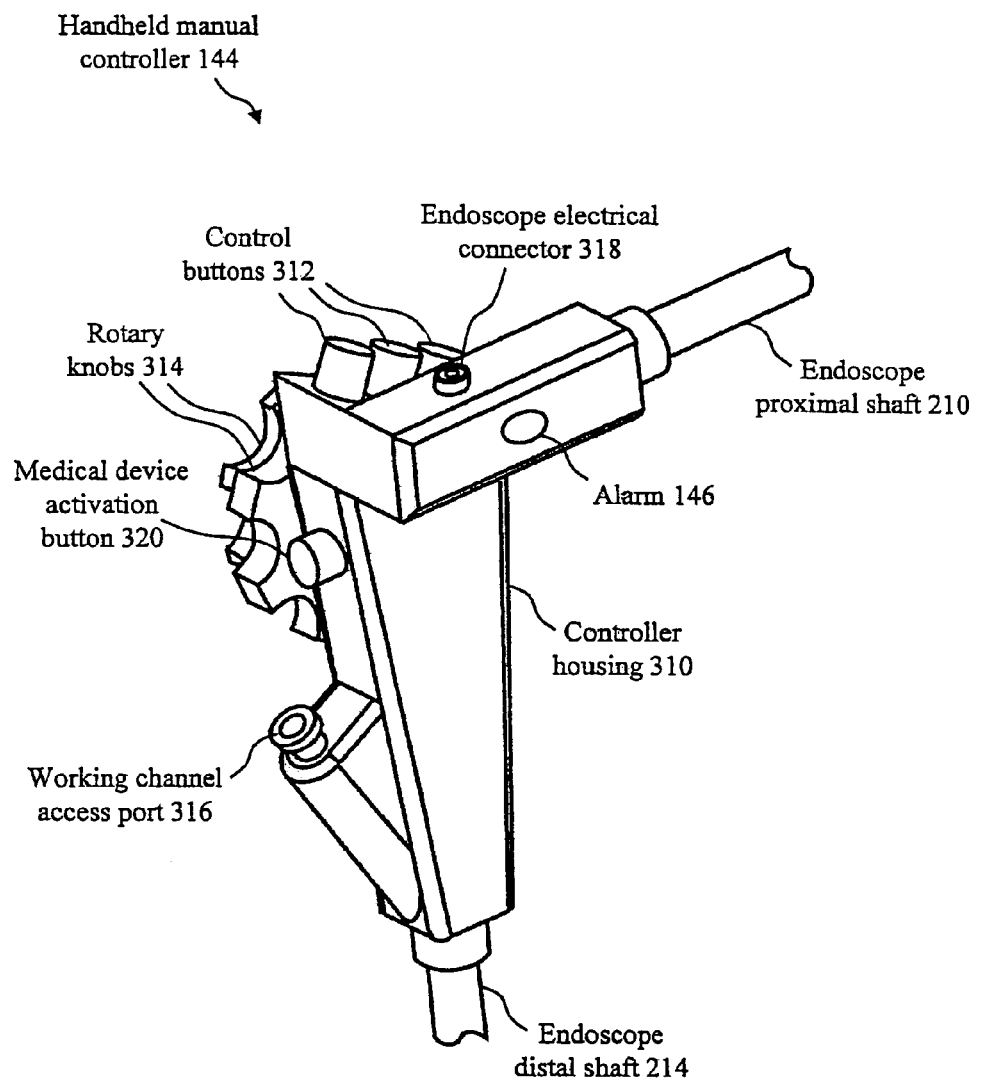
FIG. 3 illustrates a perspective view of a handheld manual controller of an imaging endoscope in accordance with an embodiment of the present invention.

FIG. 3 illustrates a perspective view of handheld manual controller 144 in accordance with an embodiment of the invention. FIG. 3 shows that handheld manual controller 144 includes a controller housing 310 formed of a suitably lightweight, rigid material, such as molded plastic. Controller housing 310 is electrically, mechanically, and fluidly connected, at one end, to endoscope proximal shaft 210 and, at an opposite end, to endoscope distal shaft 214. Mounted within controller housing 310 of handheld manual controller 144 is a plurality of control buttons 312 that allow the physician to manipulate the functions of the endoscope, such as taking a picture, activating light, activating water, activating air, or activating suction at endoscope distal tip 216; a plurality of rotary knobs 314 for controlling the articulation of endoscope distal tip 216 for advancing into the patient; a working channel access port 316 that allows the insertion of any therapeutic or diagnostic instruments into the working channel of endoscope distal shaft 214; an endoscope electrical connector 318 that provides a conveniently located electrical connection mechanism for connecting signal I/O and power of electrosurgical device 128 to operator console 110; and a medical device activation button 320 for activating electrosurgical generator 132 which supplies current to electrosurgical device 128. Additionally, mounted within controller housing 310 of handheld manual controller 144 is alarm 146, as described in more detail in reference to FIG. 1.

Medical device activation button 320 is a conveniently located mechanism for activating electrosurgical generator 132. Medical device activation button 320 replaces, for example, a separate foot pedal device, which, typically, is not conveniently located and may be cumbersome to operate in conjunction with typical endoscopic systems.

Handheld manual controller 144 is a handheld controller that accepts inputs from a human operator via standard control buttons 312, rotary knobs 314, medical device activation button 320 or other activation devices, either singularly or in combination, in order to control the operation of imaging endoscope 126 and electrosurgical device 128. Handheld manual controller 144 may optionally provide a ground connection port (not shown) for connecting grounding pad 116. Alternatively or additionally to rotary knobs 314 (and control buttons 312 and medical device activation button 320), handheld manual controller 144 may include a multi-positional switch, or a joy-stick type switch, to control the orientation or articulation of endoscope distal tip 216 or to activate various functions of the endoscope or the electrosurgical medical device. Some exemplary embodiments of a multi-positional switch suitable for use in the present invention are disclosed in the '007 patent application, incorporated herein by reference above. In one embodiment, such a multi-positional switch may be further configured and used to change operational settings for electrosurgical device 128, such as the energy level and time duration setting of electrosurgical generator 132.

Figure 4:
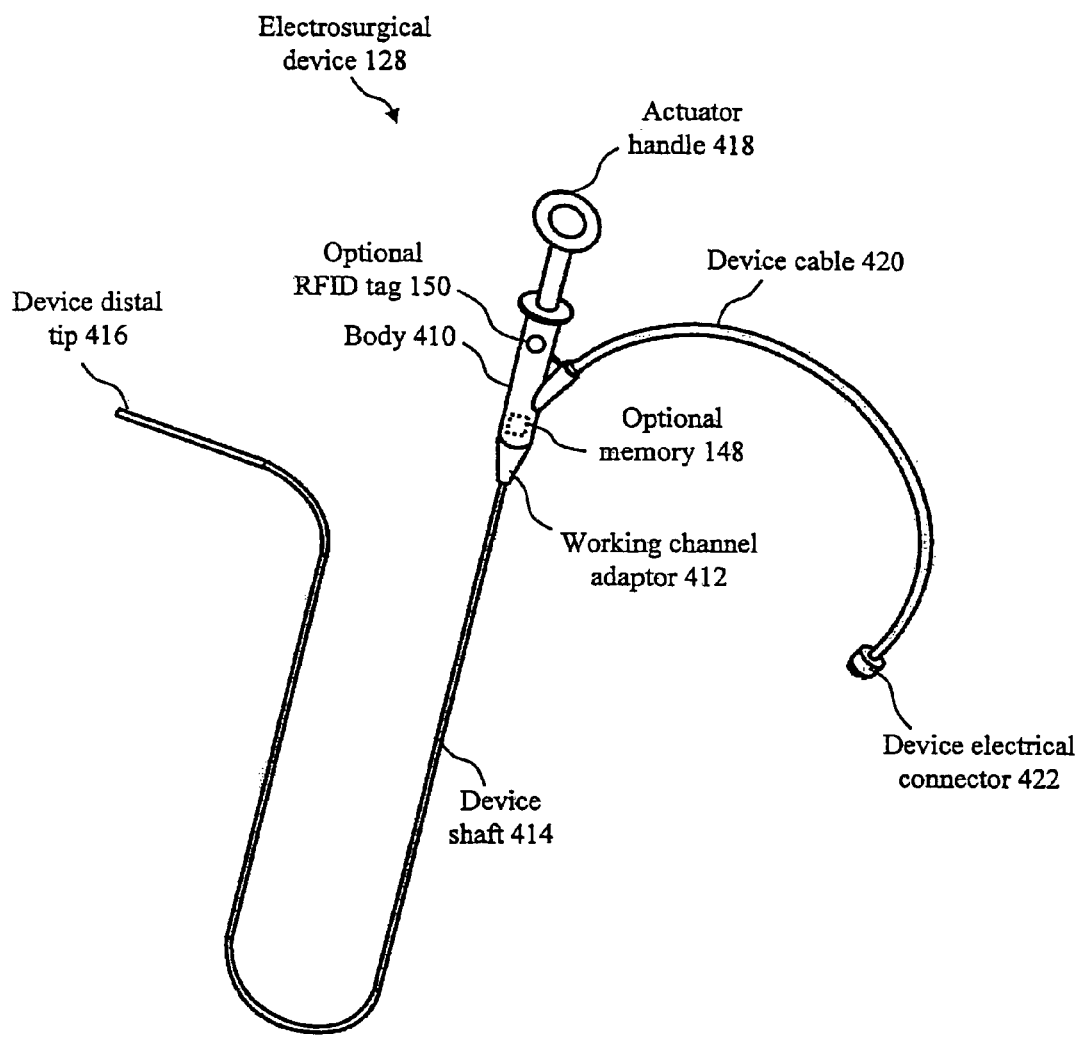
FIG. 4 illustrates a perspective view of an electrosurgical device in accordance with an embodiment of the invention.

FIG. 4 illustrates a perspective view of electrosurgical device 128 in accordance with an embodiment of the invention. Electrosurgical device 128 is representative of a typical electrosurgical medical device for inserting into the working channel of an endoscope. Example electrosurgical medical devices include, but are not limited to, a biopsy device, a snare device, a Tomes cutter, or an injection or probe device or other types of ultrasonic, or RF devices.

FIG. 4 shows that electrosurgical device 128 includes a body 410, a working channel adaptor 412 that is tapered, such that it is easily mated to working channel access port 316 of handheld manual controller 144, a device shaft 414 that has a device distal tip 416, and an actuator handle 418. Actuator handle 418 is mounted within body 410 and is used to actuate the specific instrument extending along device shaft 414 and out of device distal tip 416. Also mounted within or on body 410 may be optional memory 148 or optional RFID tag 150, as described in more detail in reference to FIG. 1. Finally, electrosurgical device 128 includes a device cable 420 that is electrically and mechanically connected, at one end, to body 410 and, at the opposite end, to a device electrical connector 422. Electrosurgical device 128 is sufficiently inexpensive to manufacture, such that it is considered a single use, disposable item.

Device electrical connector 422, at the end of device cable 420, is any standard connector that provides a convenient electrical connection mechanism for connecting signal I/O and power of electrosurgical device 128 to endoscope electrical connector 318 of handheld manual controller 144 and, subsequently, to operator console 110. The length of device cable 420 is allowed to be as suitably short as is practical, because endoscope electrical connector 318 of handheld manual controller 144, into which device electrical connector 422 is connected, is located in close proximity to electrosurgical device 128, when it is installed in imaging endoscope 126, as shown in more detail in reference to FIG. 5. The length of device cable 420 is suitably short, as compared with a typical cable needed to connect a standard electrosurgical device to a separate electrosurgical generator console, as is the case in typical endoscopic systems. As a result, cable 420, which is short in length, replaces the long, cumbersome cable of conventional devices.

Figure 5:
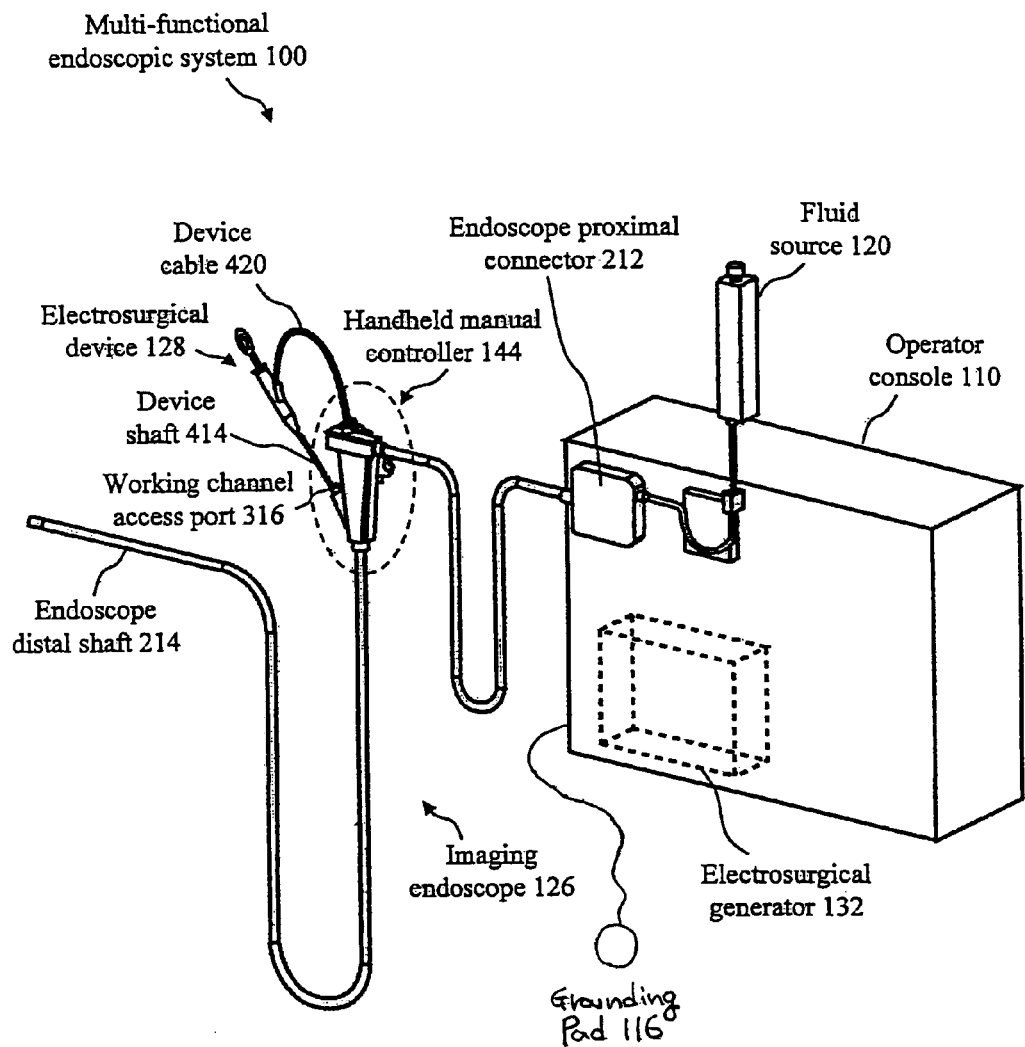
FIG. 5 illustrates a perspective view of a multi-functional endoscopic system in accordance with an embodiment of the present invention.

FIG. 5 illustrates a perspective view of an exemplary multi-functional endoscopic system 100 in accordance with the invention. More specifically, FIG. 5 shows imaging endoscope 126 and electrosurgical device 128, which are both disposable elements, in use with operator console 110. Imaging endoscope 126 is electrically and mechanically connected to the side of operator console 110 via endoscope proximal connector 212. Endoscope proximal connector 212 is for example, fluidly connected to fluid source 120 via tubing. In like manner, endoscope proximal connector 212 may be connected to vacuum source 122 (not shown) or air source 124 (not shown).

Electrosurgical device 128 is electrically and mechanically connected to imaging endoscope 126 via device electrical connector 422 (not shown) at the end of device cable 420, which plugs into endoscope electrical connector 318 (not shown) of handheld manual controller 144. The electrical/electronic connections for both imaging endoscope 126 and electrosurgical device 128 are facilitated via handheld manual controller 144 and passed onto the supporting electronics, such as electrosurgical generator 132, within operator console 110 via endoscope proximal shaft 210 (not shown) and endoscope proximal connector 212.

Additionally, FIG. 5 shows device shaft 414 of electrosurgical device 128 inserted into working channel access port 316 of handheld manual controller 144, which thereby allows device shaft 414 to pass along the length of the working channel of endoscope proximal shaft 214, such that device distal tip 416 (not shown) may extend out of endoscope distal tip 216.

With reference to FIGS. 1 through 5, an exemplary operation of multi-functional endoscopic system 100 is described as follows. A user, which may be a physician, nurse, or other assistant, attaches imaging endoscope 126 to the side of operator console 110 via endoscope proximal connector 212 and activates operator console 110. User information may be captured and stored in memory 136 via, for example, manual entry by means of keyboard 114 or downloaded from data management system 118. The user verifies that all required fluid, gas, air, or vacuum sources, such as fluid source 120, vacuum source 122, air source 124 or the like, are available. The physician introduces endoscope distal tip 216 into the patient and advances it by using rotary knobs 314 of handheld manual controller 144, until such time that the target site may be visualized upon video display 112. The appropriate type of electrosurgical device 128 is selected, depending on the medical procedure being performed. Device shaft 414 of electrosurgical device 128 is inserted into working channel access port 316 of handheld manual controller 144 and advanced, until such time that device distal tip 416 extends from endoscope distal tip 216 and is visualized upon video display 112. If electrosurgical device 128 is a monopolar device, grounding pad 116 is placed upon the patient. Device electrical connector 422 of electrosurgical device 128 is connected to endoscope electrical connector 318 on handheld manual controller 144. If optional memory 148 is present in electrosurgical device 128, console processor reads the device information and stores it in memory 136 of operator console 110. Otherwise, optional RFID tag 150 of electrosurgical device 128 may be manually scanned by optional RFID reader 140 of operator console 110, in order to obtain device information. Using the device information stored in memory 136, the default settings of the particular electrosurgical device 128 are displayed to the user via GUI 142, and the user may elect to adjust these settings. The medical procedure is then performed by the physician manipulating control buttons 312 and rotary knobs 314 of handheld manual controller 144, in order to manage the functions of imaging endoscope 126; by a nurse or assistant manipulating actuator handle 418 of electrosurgical device 128 to manipulate the actuator of electrosurgical device 128; and by the physician manipulating medical device activation button 320 of handheld manual controller 144 to activate current from electrosurgical generator 132 that drives the active element of electrosurgical device 128. After the medical procedure is completed, electrosurgical device 128 is withdrawn from imaging endoscope 126, imaging endoscope 126 is withdrawn from the patient, and endoscope proximal connector 212 of imaging endoscope 126 is disconnected from the side of operator console 110 via its quick-release mechanism. Imaging endoscope 126 and electrosurgical device 128 are properly disposed of.

Throughout the medical procedure, data is being logged in memory 136 under the control of software loaded in console processor 130. After the medical procedure is completed, the user may initiate a data transfer operation to transmit the procedure data from operator console 110 to data management system 118 for further processing. An example detailed method of using multi-functional endoscopic system 100 is described in more detail in reference to FIG. 6.

Figure 6:
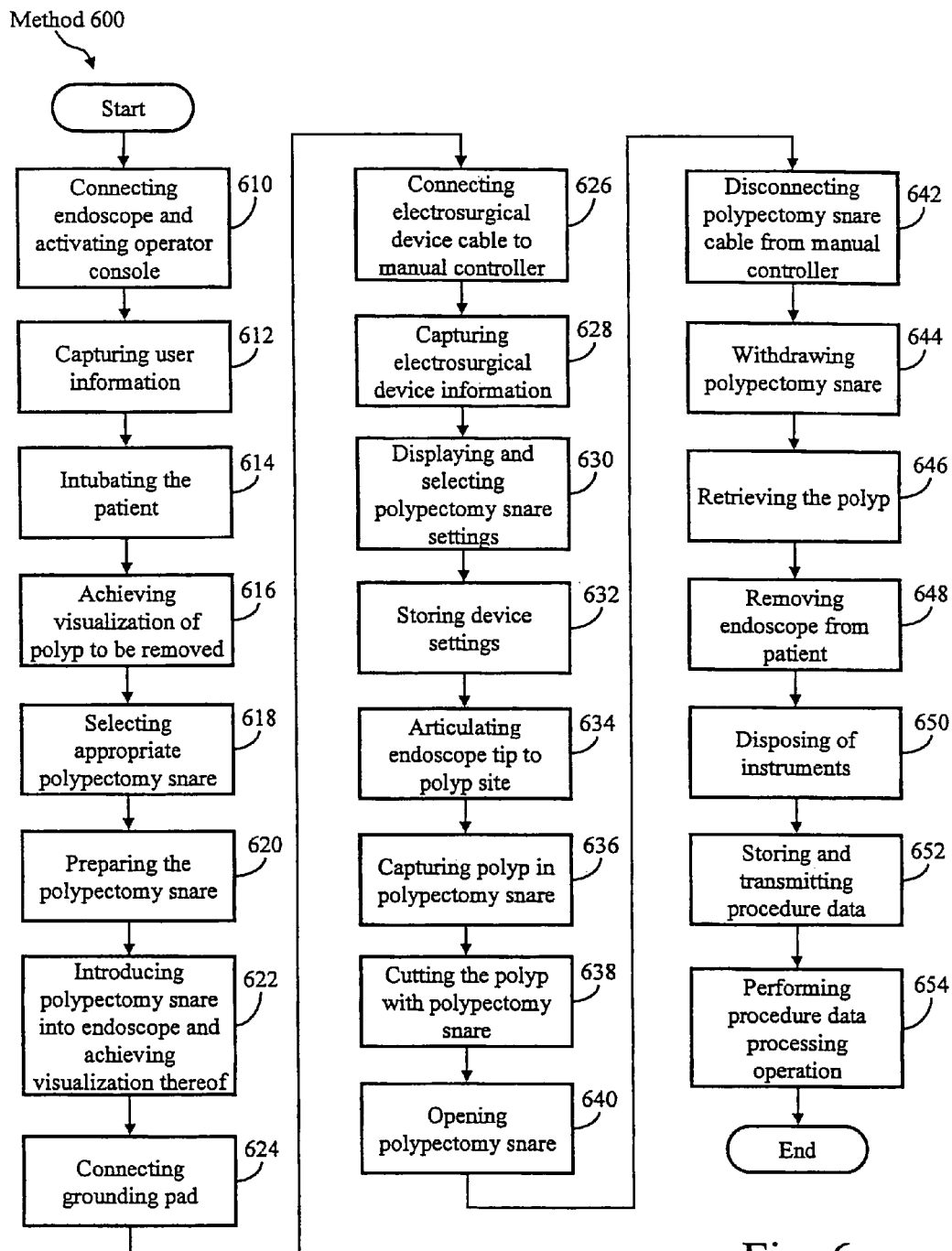
FIG. 6 illustrates a flow diagram of an example method of using a multi-functional endoscopic system in accordance with an embodiment of the present invention in a polypectomy procedure.

FIG. 6 illustrates a flow diagram of an example method 600 of using multi-functional endoscopic system 100 in a polypectomy procedure in accordance with an embodiment of the invention. Method 600 and multi-functional endoscopic system 100 are not limited to a polypectomy procedure. Those skilled in the art will recognize that the method steps of method 600 may be adapted easily to apply to any of the various medical procedures that use the various types of electrosurgical devices, respectively. Method 600 includes the steps of:

Step 610: Connecting Endoscope and Activating Operator Console

In this step, a user, which may be a physician, nurse, or other assistant, attaches endoscope proximal connector 212 of imaging endoscope 126 to the side of operator console 110 and activates operator console 110. Method 600 proceeds to step 612.

Step 612: Capturing User Information

In this step, user information, such as the user's name, is captured and stored in memory 136 via, for example, manual entry upon keyboard 114 or downloaded from data management system 118. Method 600 proceeds to step 614.

Step 614: Intubating the Patient

In this step, the physician intubates the patient, by introducing and advancing endoscope distal tip 216 of imaging endoscope 126 into a body cavity of the patient. Method 600 proceeds to step 616.

Step 616: Achieving Visualization of Polyp to be Removed

In this step, the physician advances endoscope distal tip 216 of imaging endoscope 126 into the patient, by using control buttons 312 and rotary knobs 314 of handheld manual controller 144, until such time that the polyp to be removed is visualized at endoscope distal tip 216 and the image is displayed to the user upon video display 112. Method 600 proceeds to step 618.

Step 618: Selecting Appropriate Polypectomy Snare

In this step, the physician selects the appropriate type of electrosurgical device 128. In this example, an electrosurgical device 128 that includes a polypectomy snare of the desired size is selected, based upon the size of the polyp to be removed. Method 600 proceeds to step 620.

Step 620: Preparing the Polypectomy Snare

In this step, the user unwraps the selected electrosurgical device 128 from its packaging and, by opening and closing electrosurgical device 128 by using actuator handle 418, verifies that electrosurgical device 128 is operational. Method 600 proceeds to step 622.

Step 622: Introducing Polypectomy Snare into Endoscope and Achieving Visualization Thereof In this step, the user inserts device shaft 414 of electrosurgical device 128 into working channel access port 316 of handheld manual controller 144 and advances device shaft 414, until such time that device distal tip 416 is fully captured in the field of view, while extended 5-10 mm from endoscope distal tip 216. The image is displayed to the user upon video display 112. Method 600 proceeds to step 624.

Step 624: Connecting Grounding Pad

In this step, because electrosurgical device 128 is a monopolar device, the user places grounding pad 116 upon the patient and connects grounding pad 116 to operator console 110 or, alternatively, to a ground port on handheld manual controller 144. Method 600 proceeds to step 626.

Step 626: Connecting Electrosurgical Device Cable to Manual Controller

In this step, the user connects electrosurgical device 128 to imaging endoscope 126, by plugging device electrical connector 422 of electrosurgical device 128 into endoscope electrical connector 318 on handheld manual controller 144 and thereby achieving an electrical connection to the electrical/electronic support electronics, e.g., electrosurgical generator 132, within operator console 110. Furthermore, handheld manual controller 144 and operator console 110 are the user interface for electrosurgical device 128. Method 600 proceeds to step 628.

Step 628: Capturing Electrosurgical Device Information

In this step, if optional memory 148 is present in electrosurgical device 128, console processor 130 reads the device information, such as the device type and its default settings, from optional memory 148 of electrosurgical device 128 and stores it in memory 136 of operator console 110. Otherwise, optional RFID tag 150 of electrosurgical device 128 may be scanned manually by optional RFID reader 140 of operator console 110, in order to obtain device information. Method 600 proceeds to step 630.

Step 630: Displaying and Selecting Polypectomy Snare Settings

In this step, under the control of console processor 130, the default settings and/or physician-specific settings of electrosurgical device 128 are displayed to the user via GUI 142. The physician-specific preferences are available to the console via a connection to the centralized data management system 118. Subsequently, the user may elect to use the default settings, the physician-specific settings, or to adjust the settings. The adjustment of settings may be performed by using any type of user input device, such as a touch screen provided as part of GUI 142 of video display 112, keyboard 114, or by using a multi-positional switch (i.e., joy-stick type switch), as described above. Settings include, for example, the energy level and time duration setting of electrosurgical generator 132. Method 600 proceeds to step 632.

Step 632: Storing Device Settings

In this step, under the control of console processor 130, the selected device settings of electrosurgical device 128 are stored in memory 136 in console processor 130. Method 600 proceeds to step 634.

Step 634: Articulating Endoscope Tip to Polyp Site

In this step, the physician articulates endoscope distal tip 216 into the patient and advances it to the polyp to be removed, by manipulating control buttons 312 and rotary knobs 314 of handheld manual controller 144, which manage the functions of imaging endoscope 126. Method 600 proceeds to step 636.

Step 636: Capturing Polyp in Polypectomy Snare

In this step, while the physician maintains the angulation to the polyp to be removed, a nurse or assistant opens and closes the polypectomy snare of electrosurgical device 128, by using actuator handle 418, and thereby grasps the polyp to be removed. Method 600 proceeds to step 638.

Step 638: Cutting the Polyp with Polypectomy Snare

In this step, the physician presses medical device activation button 320 of handheld manual controller 144 to activate current from electrosurgical generator 132 that energizes the polypectomy snare element of electrosurgical device 128, in order to sever the base of the polyp from the tissue wall. Method 600 proceeds to step 640.

Step 640: Opening Polypectomy Snare

In this step, a nurse or assistant opens the polypectomy snare of electrosurgical device 128, by using actuator handle 418, and thereby releasing the polyp. Method 600 proceeds to step 642.

Step 642: Disconnecting Electrosurgical Device Cable from Manual Controller

In this step, the user disconnects electrosurgical device 128 from imaging endoscope 126 by unplugging device electrical connector 422 of electrosurgical device 128 from endoscope electrical connector 318 on handheld manual controller 144. Method 600 proceeds to step 644.

Step 644: Withdrawing Polypectomy Snare

In this step, the user withdraws device shaft 414 of electrosurgical device 128 from the working channel of imaging endoscope 126. Method 600 proceeds to step 646.

Step 646: Retrieving the Polyp

In this step, a removal instrument, such as biopsy forceps or a retrieval basket, is inserted into the working channel of imaging endoscope 126 to retrieve the polyp. Alternatively, the polyp is captured against the surface of endoscope distal tip 216 by the polypectomy snare of electrosurgical device 128 and retrieved at the same time that endoscope distal shaft 214 is withdrawn from the patient in step 648. Method 600 proceeds to step 648.

Step 648: Removing Endoscope from Patient

In this step, the user withdraws endoscope distal shaft 214 of imaging endoscope 126 from the patient. Method 600 proceeds to step 650.

Step 650: Disposing of Instruments

In this step, the user disconnects endoscope proximal connector 212 of imaging endoscope 126 from the side of operator console 110 via its quick-release mechanism and imaging endoscope 126 and electrosurgical device 128 are properly disposed of. Method 600 proceeds to step 652.

Step 652: Storing and Transmitting Procedure Data

In this step, after the medical procedure is completed, the user may initiate a data transfer operation to transmit the procedure data, which has been stored in memory 136 under the control of software loaded in console processor 130 throughout the procedure, from operator console 110 to data management system 118 for further processing. Data includes, for example, the type of medical procedure, the physician performing the procedure, the type of electrosurgical device 128, and all device settings, such as the energy level and time duration setting of electrosurgical generator 132. Method 600 proceeds to step 654.

Step 654: Performing Procedure Data Processing Operation

In this step, a user or other personnel accesses the procedure data stored on data management system 118 and generates a procedure report or performs any other desired data processing function. Method 600 ends.

With continuing reference to method 600 of FIG. 6, the physician may, optionally, operate both imaging endoscope 126 and electrosurgical device 128 without the need for an assistant. Furthermore, device shaft 414 of electrosurgical device 128 may, optionally, be preloaded through working channel access port 316 of handheld manual controller 144 and, thus, into the working channel of imaging endoscope 126.

Figure 7:
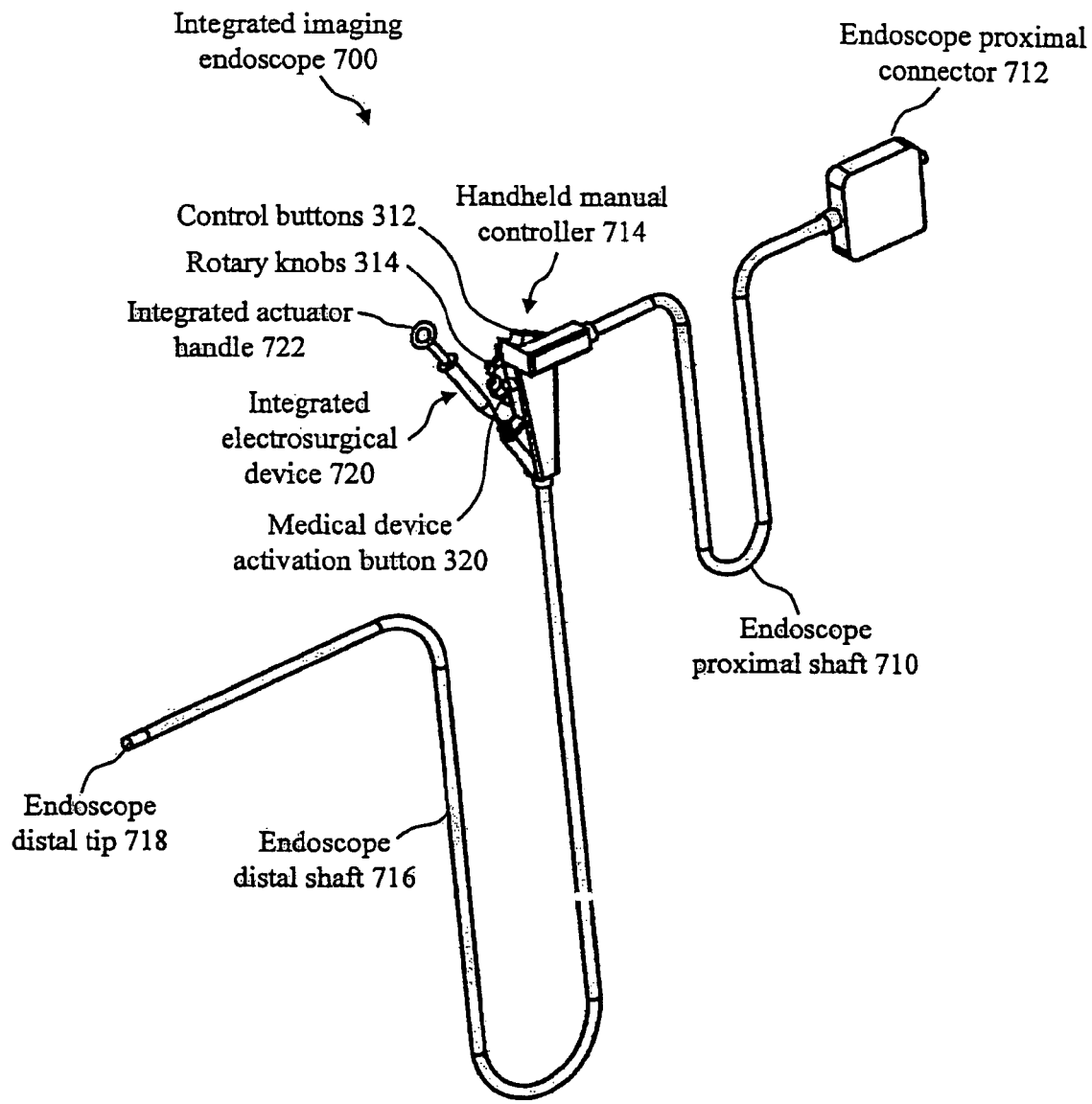
FIG. 7 illustrates a perspective view of an integrated imaging endoscope in accordance with an embodiment of the invention.

FIG. 7 illustrates a perspective view of an integrated imaging endoscope 700 in accordance with another embodiment of the invention. Integrated imaging endoscope 700 provides the combined functions of imaging endoscope 126 of FIG. 2 and electrosurgical device 128 of FIG. 4, integrated into one apparatus. As a result, integrated imaging endoscope 700 is suitable for use in multi-functional endoscopic system 100 of FIGS. 1 and 5, as a direct replacement for imaging endoscope 126 and electrosurgical device 128. Integrated imaging endoscope 700 is sufficiently inexpensive to manufacture, such that it is considered a single use, disposable item.

Integrated imaging endoscope 700 includes an endoscope proximal shaft 710 that is electrically, mechanically, and fluidly connected, at one end, to an endoscope proximal connector 712 and, at an opposite end, to a port of a handheld manual controller 714. Imaging endoscope 700 further includes an endoscope distal shaft 716 that is electrically, mechanically, and fluidly connected, at one end, to a port of handheld manual controller 714 and has an endoscope distal tip 718, located at its opposite end, for advancing into a patient's body cavity. The housing of handheld manual controller 714 includes control buttons 312, rotary knobs 314, and medical device activation button 320, as described in more detail in reference to FIG. 3.

The housing of endoscope proximal connector 712 is formed of a suitably lightweight, rigid material, such as molded plastic. Endoscope proximal connector 712 provides a quick-release mechanism for making and breaking all electrical, mechanical, and fluid/air/vacuum connections. The quick-release mechanism allows endoscope proximal connector 712 to be secured easily to the exterior of operator console 110. Endoscope proximal connector 712 includes wires and tubes that pass through endoscope proximal shaft 710, then through handheld manual controller 714, then through endoscope distal shaft 716, and then to endoscope distal tip 718.

Endoscope proximal shaft 710 and endoscope distal shaft 716 are formed of a suitably lightweight, flexible material, such as polyurethane or other suitable biocompatible plastic. Endoscope proximal shaft 710 and endoscope distal shaft 716 are elongated shafts that have one or more lumens located therein and wiring located therein to support, for example, a working channel, a jet wash mechanism, an illumination mechanism, and an image sensor that are located at endoscope distal tip 718. Also included within handheld manual controller 714 and endoscope distal shaft 716 are the electrical and mechanical mechanisms for articulating endoscope distal tip 718 for advancing into a patient.

Additionally, handheld manual controller 714 of integrated imaging endoscope 700 includes an integrated electrosurgical device 720 that is manipulated via an integrated actuator handle 722. Integrated imaging endoscope 700 is, therefore, representative of a procedure-specific device, wherein a specific electrosurgical device, such as a polypectomy snare, a needle-knife, biopsy forceps, or a spatula, is manufactured directly into handheld manual controller 714 and endoscope distal shaft 716 of integrated imaging endoscope 700, rather than inserted into its working channel, which thereby leaves the working channel within endoscope distal shaft 716 available for other uses. The associated electronics of integrated electrosurgical device 720 is also integrated into integrated imaging endoscope 700 and, thus, no external electrical/electronic cable is required, as the electrical wiring is directly wired into handheld manual controller 714, through handheld manual controller 714, and through endoscope proximal connector 712, which is connected to operator console 110. Examples of devices that may be integrated into integrated imaging endoscope 700 are found in reference to FIGS. 8 through 11; however, the scope of this invention is not limited to those examples described in reference to FIGS. 8 through 11.

Figure 8:
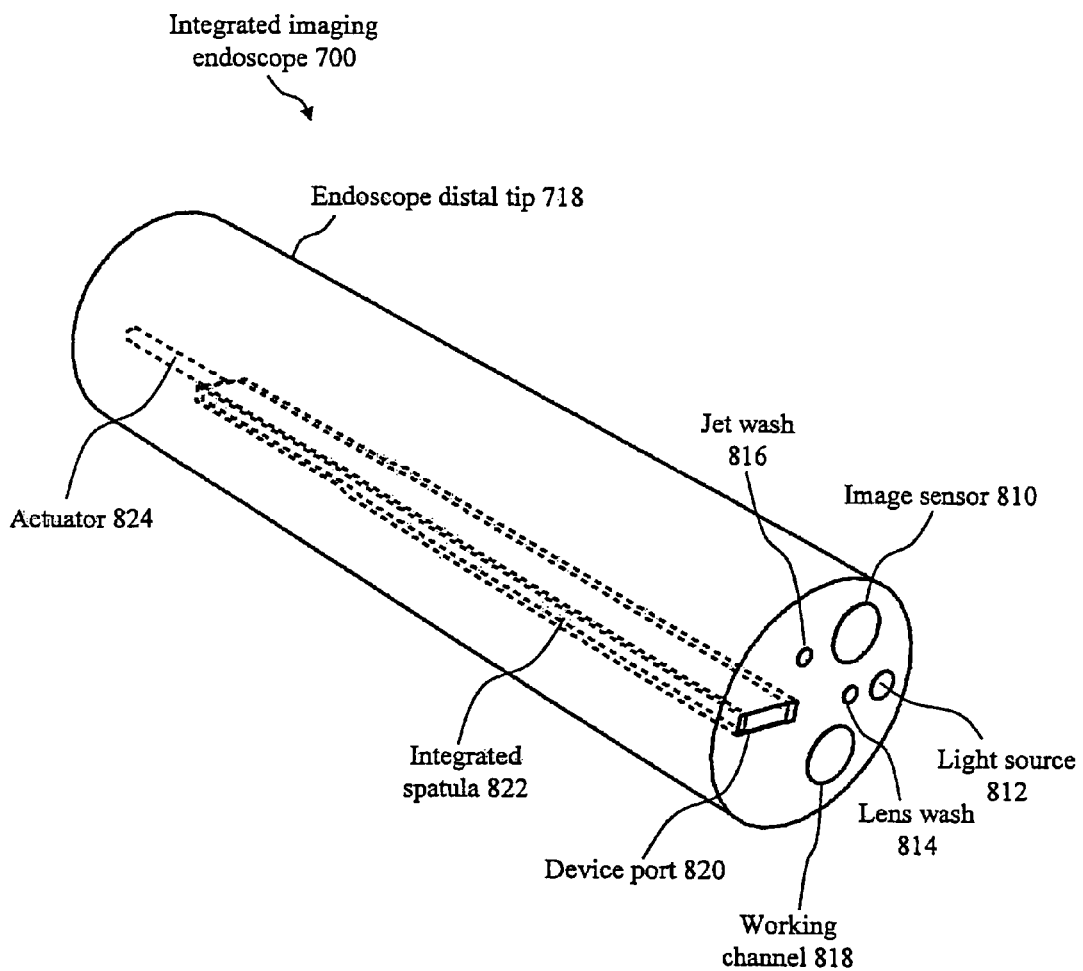
FIG. 8 illustrates a perspective view of an example integrated imaging endoscope, into which a spatula device is integrated in accordance with an embodiment of the invention.

FIG. 8 illustrates a perspective view of an example integrated imaging endoscope 700, into which a spatula device is integrated in accordance with an embodiment of the invention. Integrated imaging endoscope 700 includes instrumentation installed at endoscope distal tip 718, such as an image sensor 810, which is, for example, a complementary metal-oxide semiconductor (CMOS) chip or charge coupled device (CCD); a light source 812, which is, for example, a light-emitting diode (LED) or a fiber optic; a lens wash 814 and jet wash 816, which are fluid ports for dispensing a liquid; and a working channel 818, through which a therapeutic or diagnostic instrument may be passed.

In this example of an integrated spatula device, integrated imaging endoscope 700 further includes a device port 820, into which an integrated spatula 822 is slideably fitted, and an actuator 824, installed along the length of endoscope distal shaft 716 and connected to integrated spatula 822, at one end, and to integrated actuator handle 722, at its opposite end. To use integrated spatula 822 during a medical procedure, a user manipulates integrated actuator handle 722. Device port 820, integrated spatula 822, and actuator 824 are manufactured directly into endoscope distal shaft 716 and thereby leave working channel 818 within endoscope distal shaft 716 available for other uses, such as for irrigation, polyp retrieval, multiple biopsies, or suction, during the medical procedure.

Figure 9:
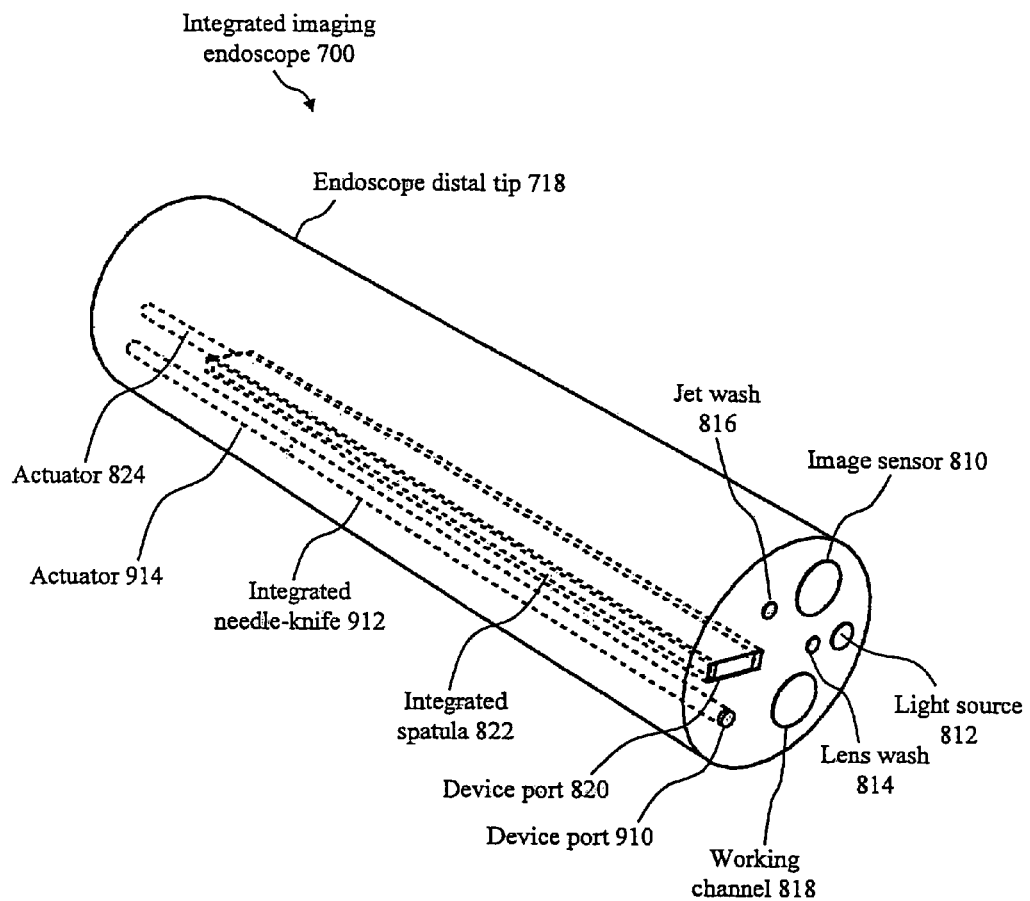
FIG. 9 illustrates a perspective view of another example of an integrated imaging endoscope, into which both a spatula and a needle-knife device are integrated in accordance with an embodiment of the invention.

FIG. 9 illustrates a perspective view of another example of integrated imaging endoscope 700, into which both a spatula and a needle-knife device are integrated in accordance with another embodiment of the invention. Integrated imaging endoscope 700 of FIG. 9 includes instrumentation installed at endoscope distal tip 718, such as image sensor 810, light source 812, lens wash 814, jet wash 816, and working channel 818, as described in more detail in reference to FIG. 8. However, integrated imaging endoscope 700 of FIG. 9 further includes another device port, a device port 910, into which an integrated needle-knife 912 is slideably fitted, and an actuator 914, installed along the length of endoscope distal shaft 716 (not shown) and connected to integrated needle-knife 912, at one end, and to another integrated actuator handle (not shown), similar to integrated actuator handle 722, at its opposite end.

To use integrated spatula 822 during a medical procedure, a user manipulates integrated actuator handle 722. Similarly, to use integrated needle-knife 912 during a medical procedure, a user manipulates its integrated actuator handle. Device port 820, integrated spatula 822, actuator 824, device port 910, and integrated needle-knife 912 and its actuator handle are manufactured directly into endoscope distal shaft 716 and thereby leave working channel 818 within endoscope distal shaft 716 available for other uses, such as for irrigation, polyp retrieval, multiple biopsies, or suction during the medical procedure.

Figure 10:
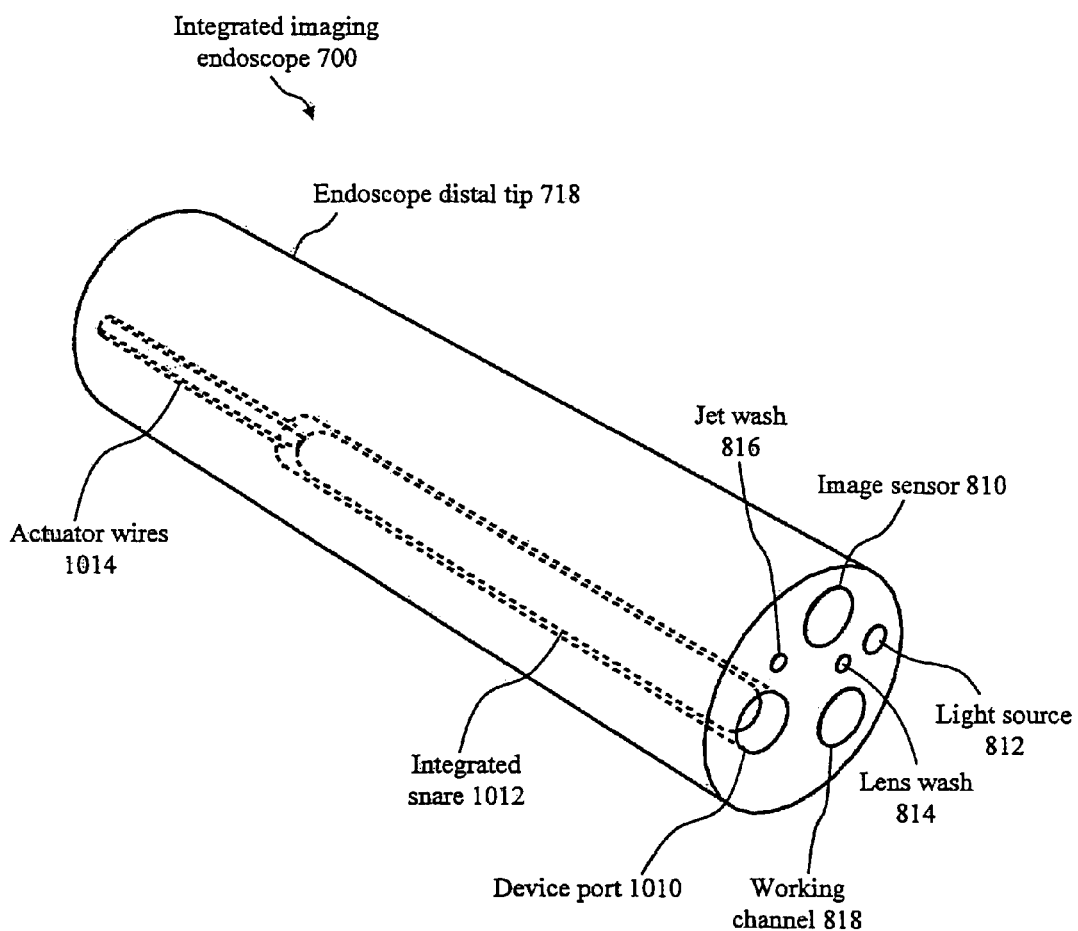
FIG. 10 illustrates a perspective view of yet another example of an integrated imaging endoscope, into which a snare is integrated in accordance with an embodiment of the invention.

FIG. 10 illustrates a perspective view of yet another example of integrated imaging endoscope 700, into which a snare is integrated in accordance with another embodiment of the invention. Integrated imaging endoscope 700 of FIG. 10 includes instrumentation installed at endoscope distal tip 718, such as image sensor 810, light source 812, lens wash 814, jet wash 816, and working channel 818, as described in more detail in reference to FIG. 8. However, integrated imaging endoscope 700 of FIG. 10 further includes a device port 1010, into which an integrated snare 1012 is slideably fitted, and a set of actuator wires 1014 that are installed along the length of endoscope distal shaft 716 and connected to integrated actuator handle 722.

To use integrated snare 1012 during a medical procedure, a user manipulates integrated actuator handle 722. Device port 1010, integrated snare 1012, and actuator wires 1014 are manufactured directly into endoscope distal shaft 716 and thereby leave working channel 818 within endoscope distal shaft 716 available for other uses, such as for irrigation, polyp retrieval, multiple biopsies, or suction, during the medical procedure.

Figure 11:
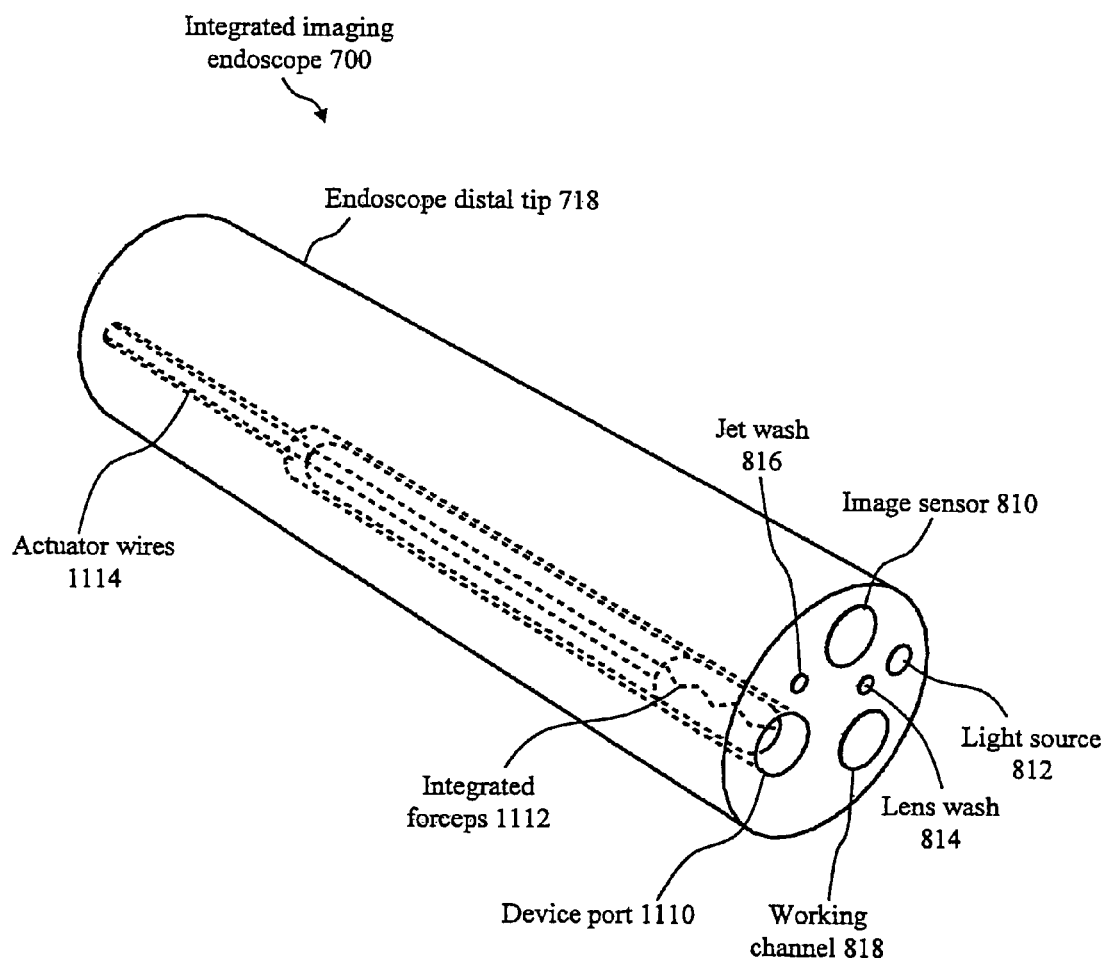
FIG. 11 illustrates a perspective view of yet another example of an integrated imaging endoscope, into which forceps are integrated in accordance with an embodiment of the invention.

FIG. 11 illustrates a perspective view of yet another example of integrated imaging endoscope 700, into which forceps are integrated in accordance with another embodiment of the invention. Integrated imaging endoscope 700 of FIG. 11 includes instrumentation installed at endoscope distal tip 718, such as image sensor 810, light source 812, lens wash 814, jet wash 816, and working channel 818, as described in more detail in reference to FIG. 8. However, integrated imaging endoscope 700 of FIG. 10 further includes a device port 1110, into which integrated forceps 1112 are slideably fitted, and a set of actuator wires 1114 that are installed along the length of endoscope distal shaft 716 and connected to integrated actuator handle 722.

To use integrated forceps 1112 during a medical procedure, a user manipulates integrated actuator handle 722. Device port 1110, integrated forceps 1112, and actuator wires 1114 are manufactured directly into endoscope distal shaft 716 and thereby leave working channel 818 within endoscope distal shaft 716 available for other uses, such as for irrigation, polyp retrieval, multiple biopsies, or suction, during the medical procedure.

With reference to FIGS. 7 through 11, other manipulation mechanisms may be integrated into the housing of handheld manual controller 714 to compliment the use of a given integrated device, such as additional push buttons, rotary knobs, slider mechanisms, motor driven mechanisms, or a clutch mechanism for allowing rotary knobs 314 to perform a dual function. An example dual function for rotary knobs 314 is, in one mode, where rotary knobs 314 are used to articulate endoscope distal tip 718, and in another mode, where rotary knobs 314 are used to manipulate, for example, integrated snare 1012 of FIG. 10.

The method of using integrated imaging endoscope 700, such as is described in reference to FIGS. 7 through 11, is generally as described in reference to method 600 of FIG. 6, but without the need for performing steps 618, 620, and 622.

Although the present embodiment of the invention has been described with respect to a surgical device that is used with a manual handle, it will be appreciated that a remotely controlled medical device such as an endoscope of the type disclosed in application Ser. Nos. 10/406,149 and 10/811,781 could be used. The operator console includes integrated equipment that operate one or more types of surgical devices and provides the necessary power and signals to the devices through an electrical connector on the endoscope. By reading a memory or an RFID tag or other device, or by the manual selection of the type of device by the physician, the console determines what type of tool is to be used and configures the electrical connector to apply the correct signals to the device. The device is plugged into the endoscope at the break out box or otherwise near the entrance of the working channel with a universal type connector that connects a variety of devices. The connector supplies the correct signals as determined by the console, so that it can be used to perform a surgical procedure.

While the preferred embodiments of the invention have been illustrated and described, it will be appreciated that various changes can be made therein without departing from the spirit and scope of the invention.

The embodiments of the invention in which an exclusive property or privilege is claimed are defined as follows:

1. A multi-functional endoscopic system, comprising:
   an operator console;
   an imaging endoscope and a removable electrosurgical device usable with the imaging endoscope, wherein the removable electrosurgical device is insertable into and removable from a lumen extending through the imaging endoscope, wherein the imaging endoscope comprises:
   an endoscope proximal connector for coupling the imaging endoscope to the operator console, wherein the operator console includes an electrosurgical generator integrated therein for the removable electrosurgical device, a processor for controlling operation of the imaging endoscope, and a connection to at least one of a fluid source, a vacuum source, and an air source; and
   a handheld controller coupled to the operator console via the endoscope proximal connector, wherein the handheld controller is configured to control the operation of the imaging endoscope, the handheld controller having at least one of a button and a switch configured to control the removable electrosurgical device, an electrical connector configured to connect the removable electrosurgical device to the operator console, and a port configured to receive the removable electrosurgical device; and
   a shaft having a first end and a second end, wherein the first end is connected to the endoscope proximal connector and the second end is connected to the handheld controller,
   wherein the endoscopic system is configured for a high-frequency electrosurgical current to flow from the electrosurgical generator to the endoscope proximal connector, along the shaft from the first end of the shaft to the second end of the shaft, through the handheld controller, to the electrical connector of the handheld controller, to the removable electrosurgical device, and through the port of the handheld controller, such that the removable electrosurgical device electrically connects to the electrosurgical generator through the handheld controller.

2. The system of claim 1, wherein the imaging endoscope is configured to be disposable after a single use.

3. The system of claim 1, wherein the endoscope proximal connector comprises a quick-release mechanism containing electrical, mechanical, and fluid connections between the imaging endoscope and the operator console.

4. The system of claim 1, wherein the removable electrosurgical device is configured to be disposable after a single use.

5. The system of claim 1, wherein the removable electrosurgical device is selected from the group consisting of a biopsy device, a snare device, a Tomes cutter, an injection device, a probe device, a needle knife device, a spatula device, a basket device, an ultrasonic device, an RF device, and an argon plasma ablation device.

6. The system of claim 1, wherein the lumen extends from the port on the handheld controller to a distal end of the imaging endoscope.

7. The system of claim 1, wherein removable electrosurgical device includes a memory containing device-type information.

8. The system of claim 1, wherein removable electrosurgical device includes a cable that is received by the electrical connector on the handheld controller of the imaging endoscope to electrically connect the electrosurgical device to the electrosurgical generator through the handheld controller.

9. The system of claim 1, wherein the handheld controller is configured to selectively activate the electrosurgical generator for the removable electrosurgical device.

10. The system of claim 9, wherein the at least one of the button and the switch accepts input from a human operator to thereby selectively activate the electrosurgical generator for the removable electrosurgical device.

11. The system of claim 1, wherein the handheld controller comprises a handheld manual controller.

12. The system of claim 1, further comprising a data management system coupled to the operator console.

13. The system of claim 1, wherein the operator console is configured to facilitate operation of the imaging endoscope.

14. The system of claim 1, wherein the electrosurgical generator is configured to use radiofrequency energy to produce cutting or coagulation in body tissue.

15. The system of claim 14, wherein the electrosurgical generator is configured to convert low-frequency alternating current to radiofrequency energy.

16. The system of claim 1, wherein the imaging endoscope is flexible for insertion into a body cavity of a patient.

17. A multi-functional endoscope system, comprising:
   an operator console that includes an electrosurgical generator integrated therein for supplying a high-frequency electrosurgical current to a removable electrosurgical device, a processor for controlling operation of the imaging endoscope, and a connection to at least one of a fluid source, a vacuum source, and an air source; and
   a multi-function imaging endoscope configured to accommodate the removable electrosurgical device, wherein the removable electrosurgical device is capable of being inserted into and removed from a lumen of the imaging endoscope, wherein the multi-function endoscope comprises:
   an endoscopic proximal connector connected to the operator console and configured to connect to the electrosurgical generator;
   a handle coupled to the operator console and connected to the electrosurgical generator via the endoscopic proximal connector, the handle having controls that operate the imaging endoscope, at least one of a button and a switch that operates the removable electrosurgical device, an electrical connector configured to connect the removable electrosurgical device to the operator console, and a port in communication with the lumen configured to receive the removable electrosurgical device; and a shaft having a first end and a second end, wherein the first end is connected to the endoscope proximal connector and the second end is connected to the handle, wherein the handle is electrically connected to the removable electrosurgical device, and wherein the endoscope system is configured for the high-frequency electrosurgical current to flow from the electrosurgical generator to the endoscope proximal connector, along the shaft from the first end of the shaft to the second end of the shaft, through the handle, to the electrical connector of the handle, to the removable electrosurgical device, and through the port of the handle.

18. The system of claim 17, wherein the operator console includes a memory that stores information including one or more of the following: user information, user preferences, type of and default settings of the removable electrosurgical device, and electrosurgical generator settings.

19. The system of claim 17, wherein the imaging endoscope includes an RFID reader and the removable electrosurgical device includes an RFID tag.

20. The system of claim 17, further comprising a video display coupled to the operator console, the video display being configured to provide a graphical representation specific to the removable electrosurgical device after the operator console determines the type of the removable electrosurgical device.

21. The system of claim 20, wherein the graphical representation specific to the removable electrosurgical device permits a user to select the energy level of the electrosurgical generator.

22. The system of claim 17, wherein the removable electrosurgical device includes a device electrical connector that mates with the electrical connector of the handle via a cable to supply current from the electrosurgical generator to the removable electrosurgical device.

23. The system of claim 17, wherein the processor is configured to execute software for operation of the imaging endoscope, the processor and electrosurgical generator of the operator console comprising a single operational unit.

24. The system of claim 23, wherein the processor is configured to control the operation of the electrosurgical generator.

25. The system of claim 24, wherein the processor is configured to control an energy level or a time duration setting of the electrosurgical generator.

26. The system of claim 17, wherein the imaging endoscope is flexible for insertion into a body cavity of a patient.

* * * * *

UNITED STATES PATENT AND TRADEMARK OFFICE
CERTIFICATE OF CORRECTION

| | | |
|---|---|---|
| PATENT NO. | : 8,357,148 B2 | Page 1 of 1 |
| APPLICATION NO. | : 11/238649 | |
| DATED | : January 22, 2013 | |
| INVENTOR(S) | : Boulais et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 569 days.

Signed and Sealed this
Eighteenth Day of November, 2014

Michelle K. Lee
*Deputy Director of the United States Patent and Trademark Office*